United States Patent
Cam et al.

(10) Patent No.: US 9,192,388 B2
(45) Date of Patent: Nov. 24, 2015

(54) VASCULAR REMODELING DEVICE

(75) Inventors: Anh Cam, Carlsbad, CA (US); Michael Louis Losordo, San Juan Capistrano, CA (US); Jianlu Ma, Irvine, CA (US); Victoria Schuman, Minneapolis, MN (US); Xiaoling Zhao, Irvine, CA (US)

(73) Assignee: Covidien LP, Mansfield, MA (US)

( * ) Notice: Subject to any disclaimer, the term of this patent is extended or adjusted under 35 U.S.C. 154(b) by 612 days.

(21) Appl. No.: 13/473,832

(22) Filed: May 17, 2012

(65) Prior Publication Data

US 2012/0296361 A1    Nov. 22, 2012

Related U.S. Application Data

(60) Provisional application No. 61/488,127, filed on May 19, 2011.

(51) Int. Cl.

| A61F 2/954 | (2013.01) |
| A61F 2/852 | (2013.01) |
| A61B 17/12 | (2006.01) |
| A61F 2/856 | (2013.01) |
| A61F 2/82  | (2013.01) |

(52) U.S. Cl.
CPC ....... *A61B 17/1214* (2013.01); *A61B 17/12118* (2013.01); *A61F 2/852* (2013.01); *A61F 2/856* (2013.01); *A61F 2/954* (2013.01); *A61F 2002/823* (2013.01); *A61F 2002/826* (2013.01); *A61F 2230/005* (2013.01); *A61F 2230/0067* (2013.01); *A61F 2230/0097* (2013.01); *A61F 2250/0023* (2013.01)

(58) Field of Classification Search
CPC ............... A61F 2/89; A61F 2002/065; A61F 2002/823; A61F 2002/828; A61F 2210/0004; A61F 2220/0025; A61F 2002/016; A61F 2002/061; A61F 2002/067; A61F 2002/821; A61F 2002/9511; A61F 2230/0054; A61B 17/12022; A61B 17/12113; A61B 17/1214; A61B 17/12118
USPC ......................................................... 606/200
See application file for complete search history.

(56) References Cited

U.S. PATENT DOCUMENTS

| 6,210,433 B1* | 4/2001 | Larre ................ 623/1.15 |
| 7,022,132 B2* | 4/2006 | Kocur ............... 623/1.11 |
| 8,128,685 B2* | 3/2012 | Das .................. 623/1.35 |
| 2003/0055490 A1* | 3/2003 | Roubin et al. ........ 623/1.17 |
| 2007/0219619 A1* | 9/2007 | Dieck et al. ......... 623/1.13 |
| 2008/0027481 A1* | 1/2008 | Gilson et al. ........ 606/200 |

* cited by examiner

*Primary Examiner* — Sarah W Aleman
(74) *Attorney, Agent, or Firm* — Mark J. Kertz, Esq.

(57) ABSTRACT

A vascular remodeling device and methods for its use are provided. The device can be positionable at a junction of a bifurcation having an aneurysm and that defines afferent and efferent vessels. Ends of the device can be at least partially inserted into the aneurysm or can anchor the device by being at least partially inserted into efferent vessels. The device can act as a scaffolding to inhibit dislodging of objects out of the aneurysm. The device can permit perfusion to the efferent vessels. Embolic material can be inserted in the aneurysm before, during, and/or after positioning the device.

20 Claims, 15 Drawing Sheets

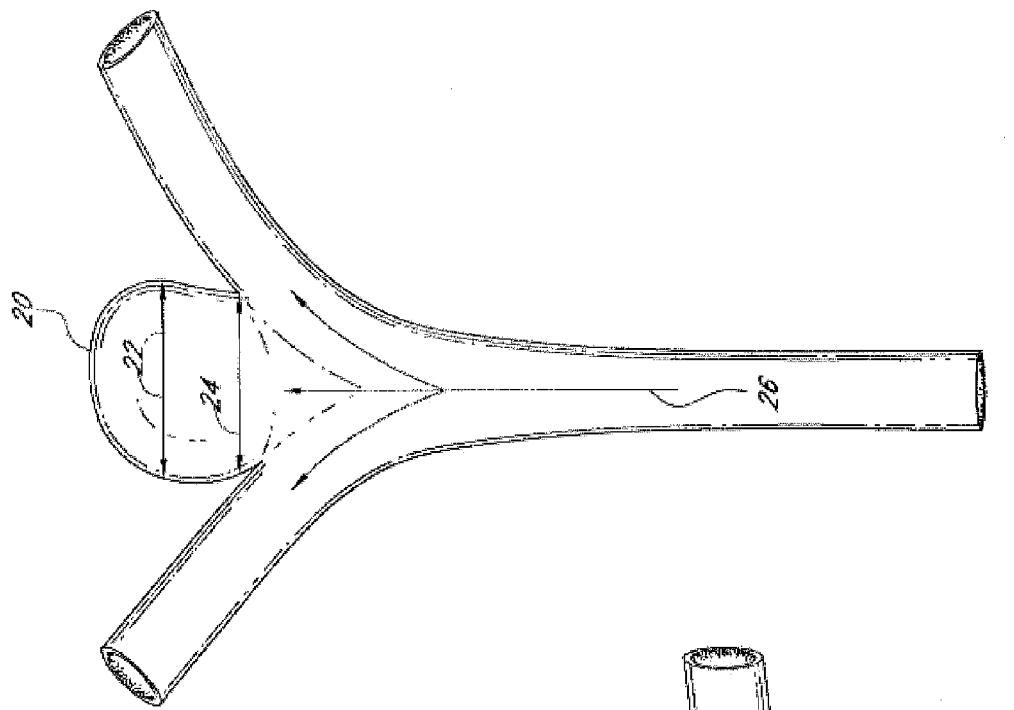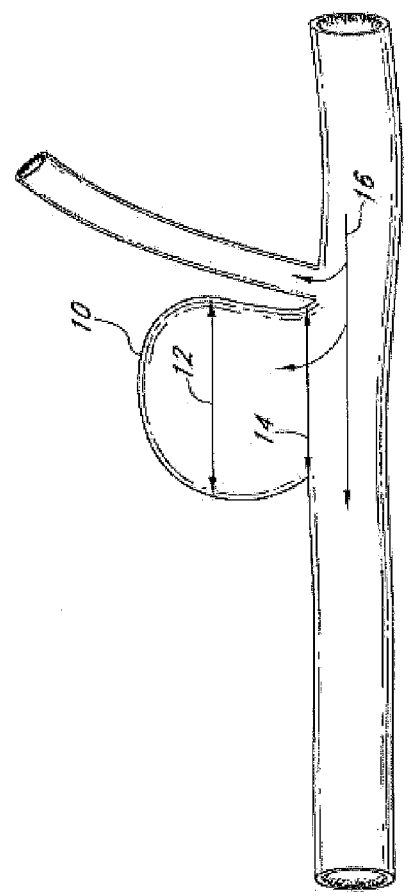
FIG. 1
FIG. 2

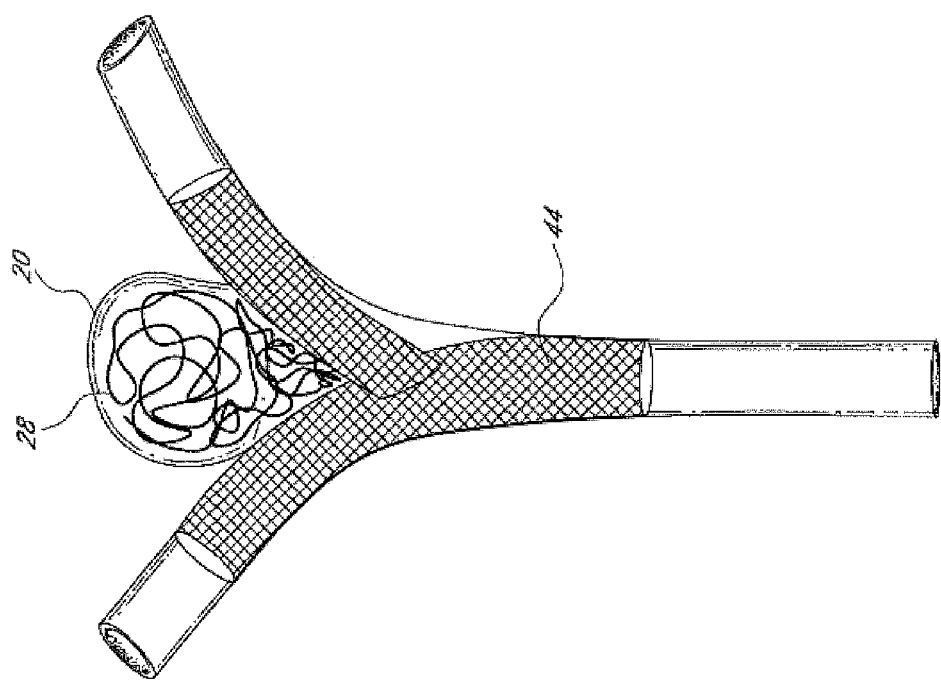

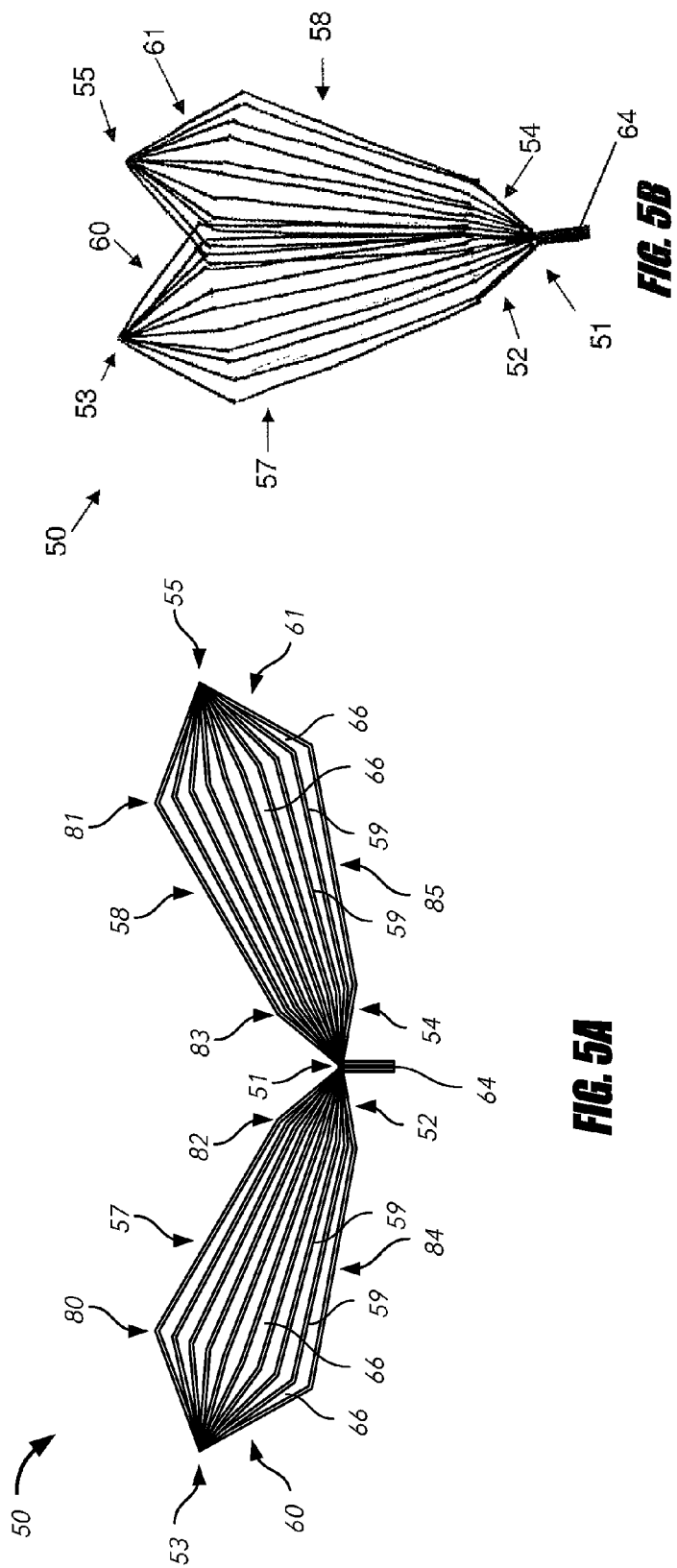

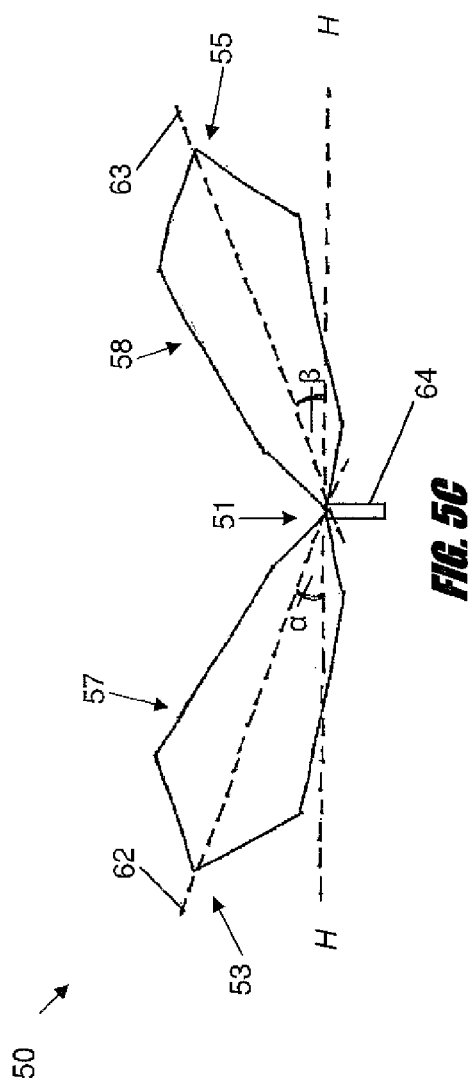
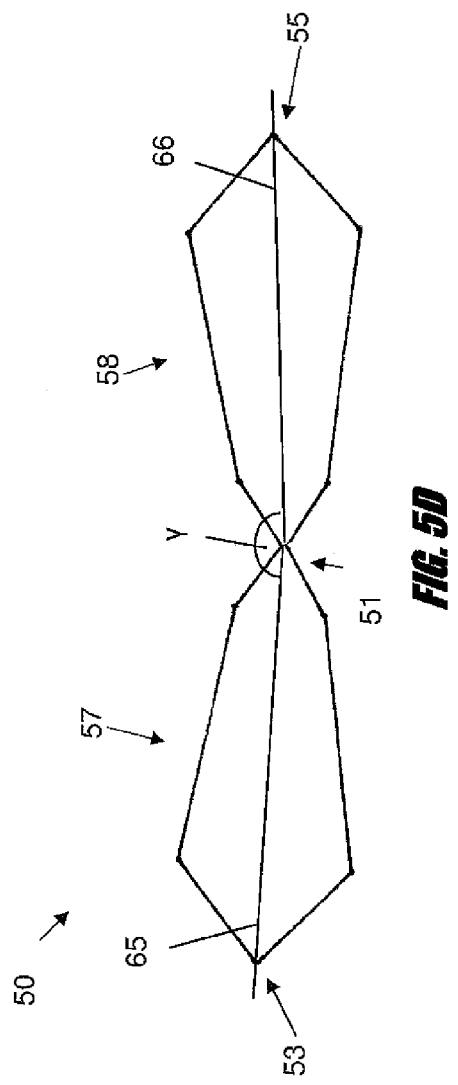

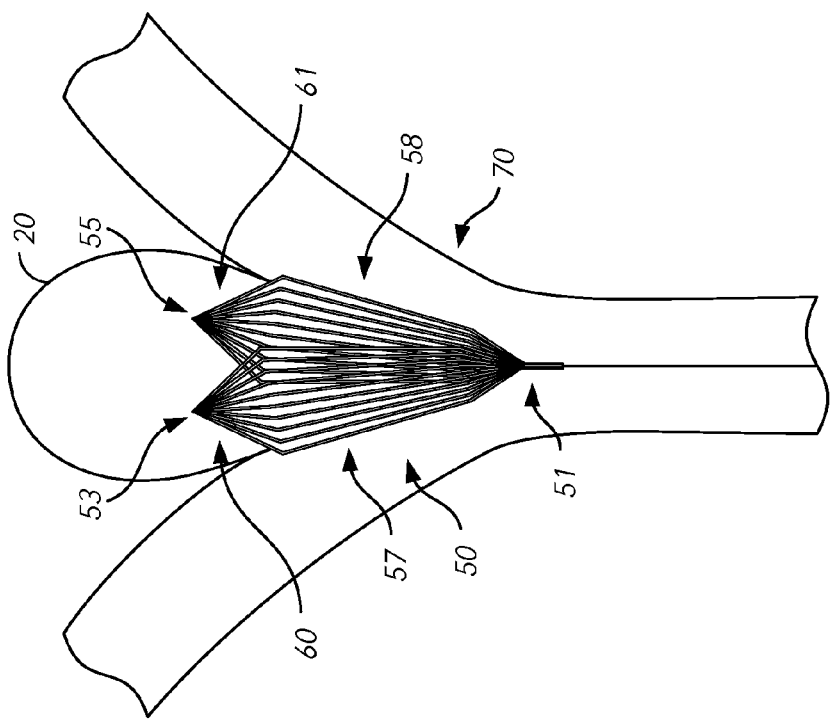
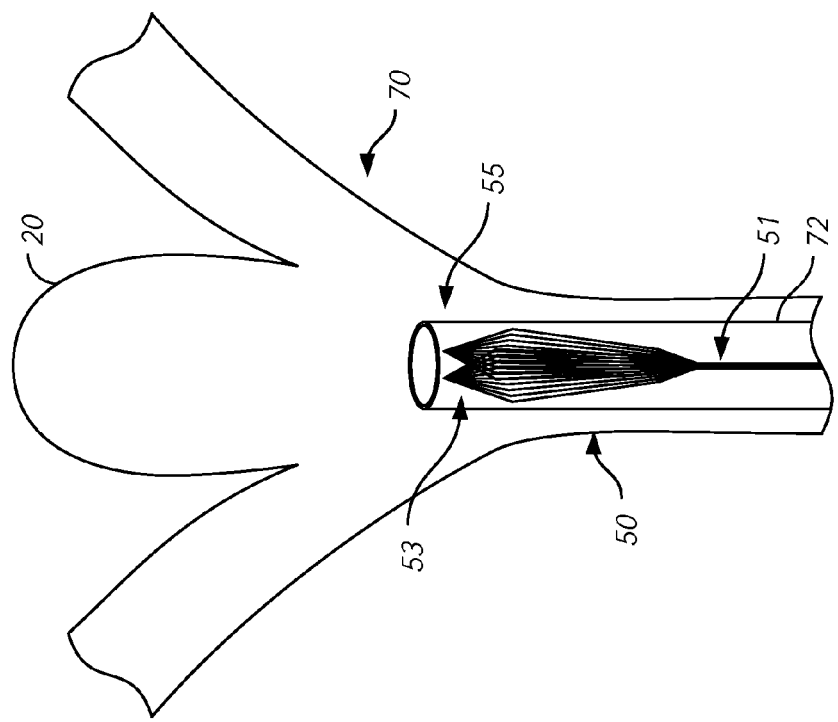

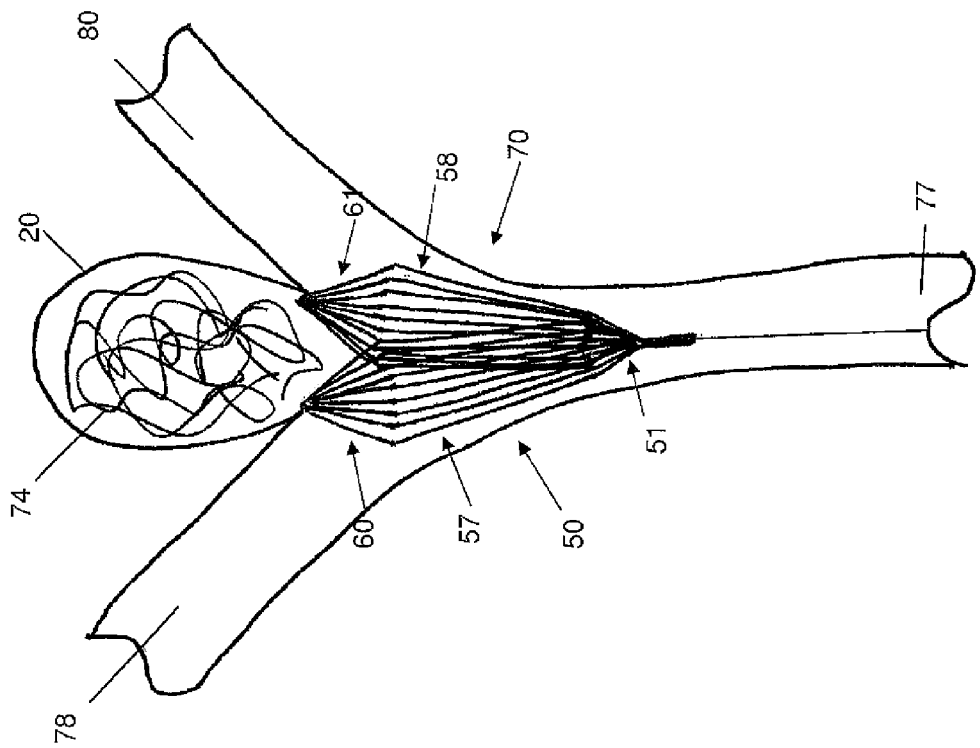
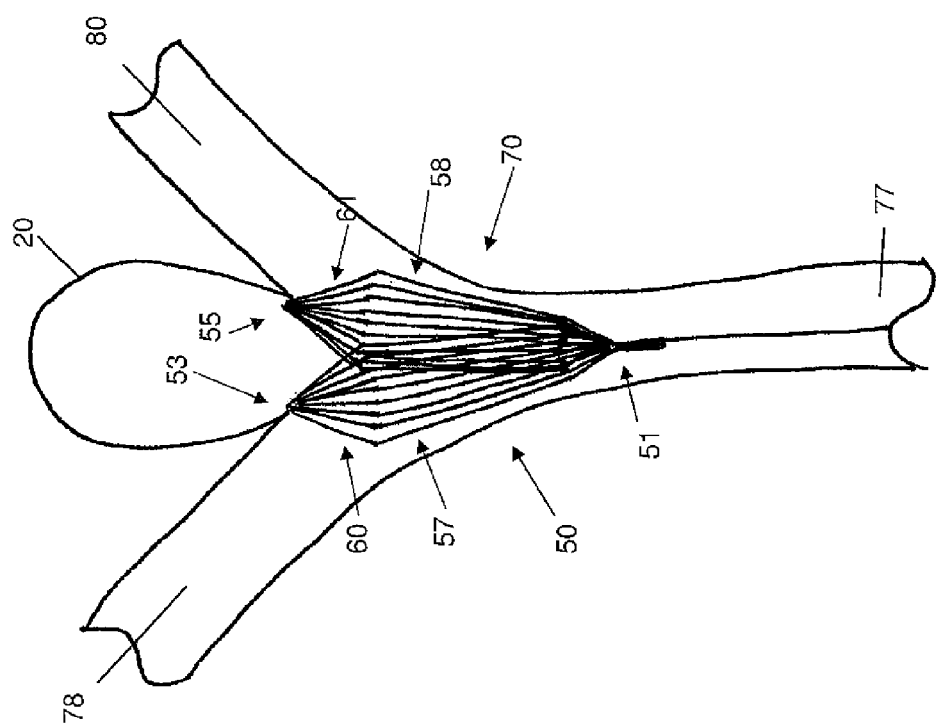
FIG. 7A
FIG. 7B

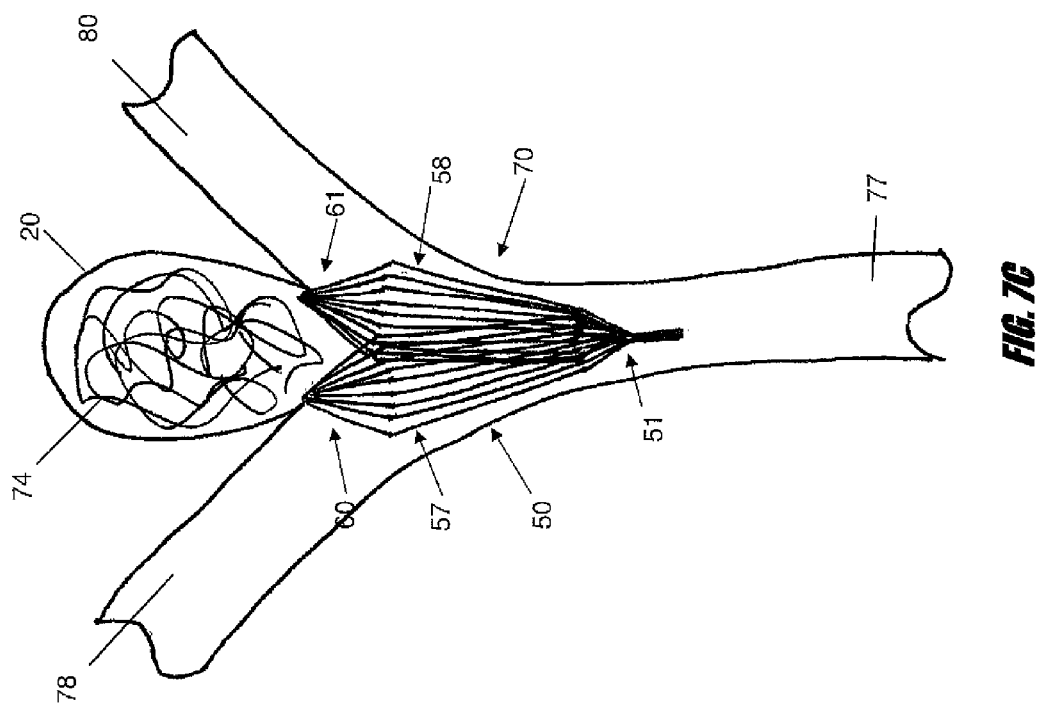

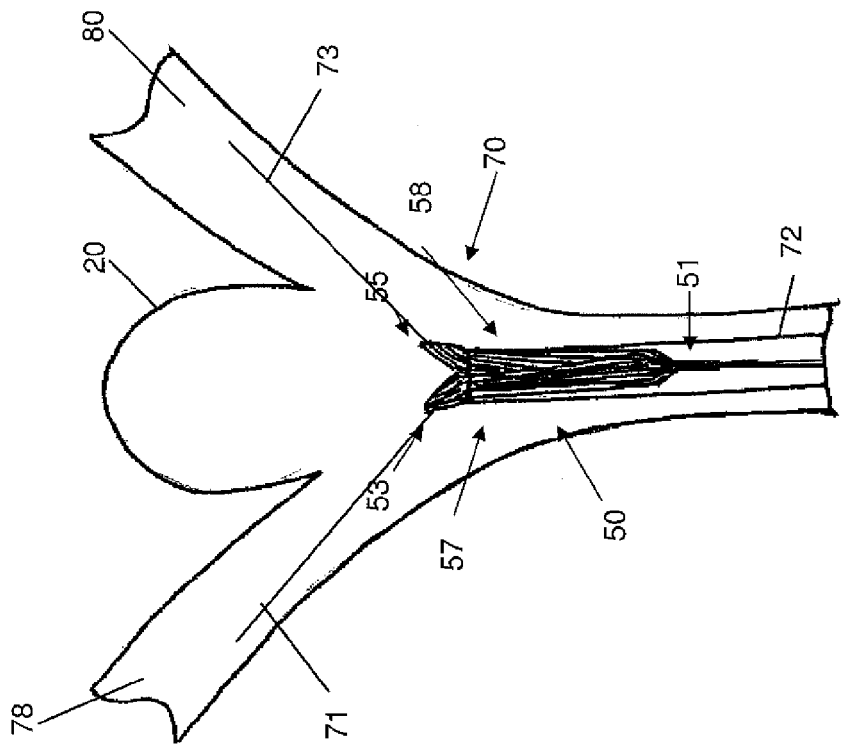
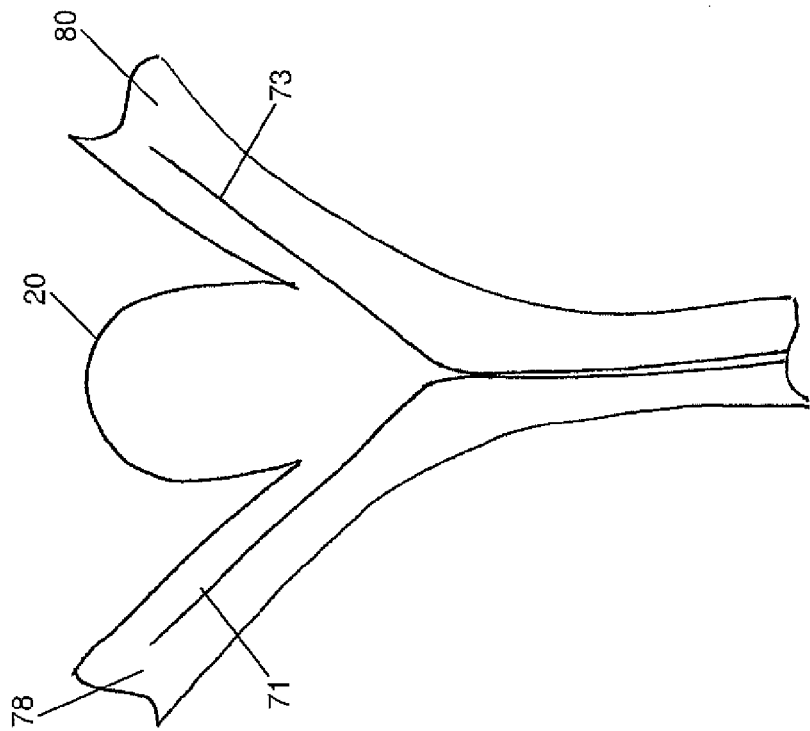

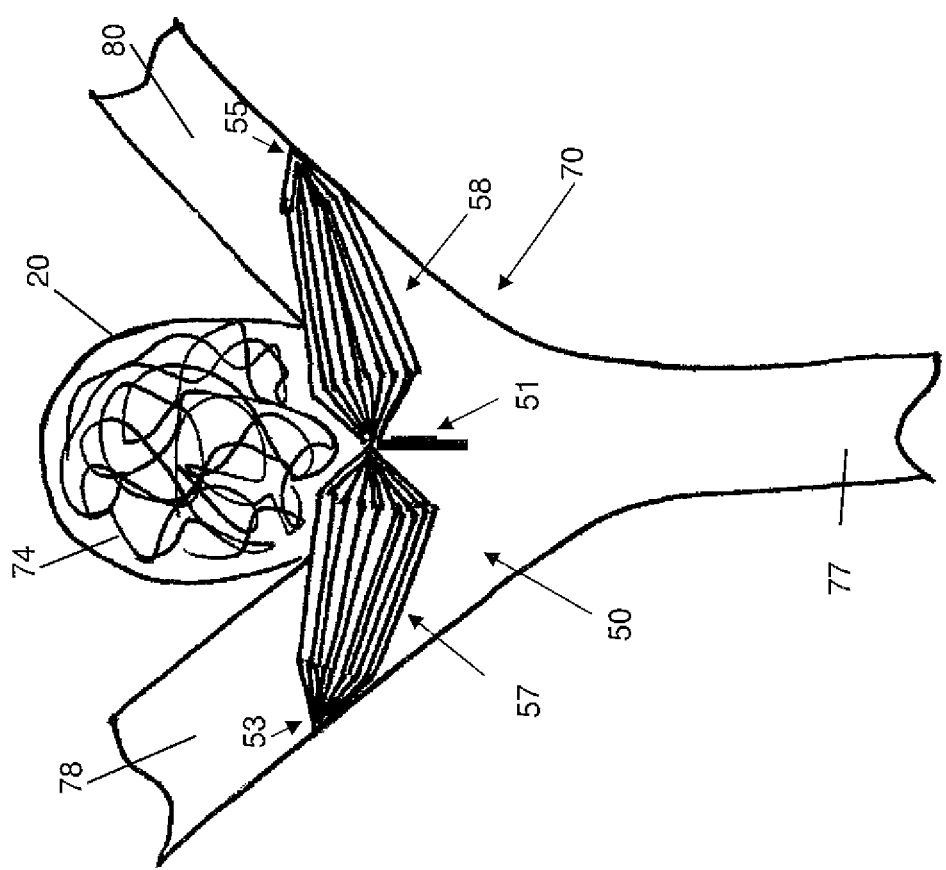

VASCULAR REMODELING DEVICE

CROSS-REFERENCE TO RELATED APPLICATIONS

This application claims the benefit of U.S. Provisional Application No. 61/488,127, filed May 19, 2011, the entirety of which is incorporated herein by reference.

BACKGROUND

1. Field

The present application generally relates to vascular remodeling devices and to the manner of their positioning in vessels, and, more particularly, to the manner of their positioning at the junction of neurovascular bifurcations having an aneurysm.

2. Description of Related Art

Neurovascular or cerebral aneurysms affect about 5% of the population. Aneurysms may be located, for example, along arterial side walls (e.g., the aneurysm 10 illustrated in FIG. 1) and at arterial bifurcations (e.g., the aneurysm 20 illustrated in FIG. 2). The direction of fluid flow is generally indicated by the arrows 16, 26. The aneurysms 10, 20 each have a fundus 12, 22, a neck 14, 24, and a fundus-to-neck ratio or "neck ratio." If the neck ratio is greater than 2 to 1 or if the neck 14, 24 is less than 4 mm, the aneurysm 10, 20 can be treated with embolization coils alone because the coils will generally constrain themselves within the aneurysm 10, 20 without dislodging into parent vessels. If the neck ratio is less than 2 to 1 or if the neck 14, 24 is greater than 4 mm, the aneurysms 10, 20 can be difficult to treat with embolization coils alone because the coils can be prone to dislodging into parent vessels, as illustrated in FIGS. 3A and 3B. Dislodging, prolapse, or herniation of coils can cause arterial occlusion, stroke, and/or death. Compared to the bifurcation illustrated in FIG. 2, the efferent vessels of the bifurcation can be at substantially different angles, have substantially different sizes, and/or be a different quantity (e.g., three or more). Compared to the bifurcation illustrated in FIG. 2, the aneurysm 20 of the bifurcation can be offset with respect to the junction (e.g., having a neck substantially open to one efferent vessel), tilted with respect to a plane created by the vessels (e.g., into or out of the page), etc. Each of these would still be accurately characterized as a "bifurcation" herein.

In order to inhibit such dislodging, tubular neck remodeling devices, for example Neuroform™, available from Boston Scientific, and Enterprise™, available from Cordis Neurovascular, can be used to keep coils or other materials within the fundus of the aneurysm and out of the vessels. Tubular remodeling devices generally consist of a braided wire or cut metallic stent or stents covering the neck of the aneurysm so that materials introduced into the fundus of the aneurysm do not dislodge out of the aneurysm.

As illustrated in FIG. 4A, tubular remodeling devices 40 are generally useful for side wall aneurysms 10. As illustrated in FIGS. 4B and 4C, tubular remodeling devices 42, 44 are generally less useful for aneurysms 20 at bifurcations, for example because shaping the remodeling devices to preserve blood flow through the afferent and efferent vessels while also inhibiting dislodging of coils 28 out of the aneurysm 20 can be difficult.

SUMMARY

In some embodiments described herein, a vascular remodeling device is provided. The vascular remodeling device can be generally bow-tie shaped. The vascular remodeling device can comprise at least two stents. The stents can be coupled at a midsection of the device. The stents can be generally diamond shaped, generally acorn shaped, generally football shaped, generally spiral shaped, etc. The stents can be hexagonally shaped in profile.

In accordance with some embodiments, a method is provided for treating an aneurysm at a junction of a bifurcation having an afferent vessel and efferent vessels. Generally, the aneurysm can have a neck and a fundus. The method can comprise the steps of advancing a delivery device or catheter proximate to the junction of the bifurcation and deploying a vascular remodeling device supported by the catheter.

A delivery device for the vascular remodeling device can include an outer sheath (e.g., a microcatheter or catheter) containing the stent in the compressed delivery state and a plunger configured to push the stent out of the outer sheath and to release the device mechanically, chemically, or electrolytically. The plunger can also include a guidewire lumen for aid in positioning of the delivery device at the treatment area.

The catheter can at least partially contain or support a vascular remodeling device in a compressed state. The device can have a first end, a second end, and a midsection. The device can be configured such that in the compressed state, the first end and the second end are distal to the midsection.

The device can be positioned at a bifurcation having an afferent vessel, efferent vessels, and an aneurysm. The method can be implemented such that the device is deployed from at least partially inside the catheter to outside the catheter at the junction of the bifurcation.

Further, during deployment, the device can self-expand to an expanded state to conform to at least one of the junction of the bifurcation or the neck of the aneurysm. During deployment, the device can expand and the stents can be biased away from one another to lock into place at the junction or across the neck of the aneurysm. The ends of the device can be positioned within the aneurysm or within the efferent vessels. The device can be configured such that it does not interfere with blood flow to efferent vessels.

Further, the device can act as a scaffolding to prevent dislodging of objects into the afferent and efferent vessels and permits perfusion of fluid to the efferent vessels.

In some embodiments, the method can be implemented to further comprise retracting the device at least partially back inside the catheter. The method can also be implemented to further comprise re-deploying the device in at least one of a second orientation or a second position. During re-deployment, the device can self-expand to the expanded state to conform to at least one of the junction of the bifurcation or the neck of the aneurysm. Additionally, the method can be implemented to comprise withdrawing the catheter and the device.

The method can also be implemented to further comprise detaching the device from the catheter. For example, the method can be implemented such that detaching the device from the catheter comprises detaching the device mechanically, electrolytically, or chemically.

In some embodiments, the method can be implemented such that embolic material can be used to treat the aneurysm using the device delivery catheter or a different catheter. According to some embodiments, the method can also be implemented such that inserting embolic material into the aneurysm occurs before deployment of the device. The method can also be implemented such that inserting embolic material into the aneurysm occurs during deployment of the device. The method can also be implemented such that inserting embolic material into the aneurysm occurs after deployment of the device. The device can be configured to reduce the effective size of the aneurysm. The device can be configured to allow insertion of embolic material therethrough.

The method can also be implemented such that inserting embolic material into the aneurysm comprises inserting embolic coils into the aneurysm. The method can also be implemented such that inserting embolic material into the aneurysm comprises inserting embolic fluid into the aneurysm.

In accordance with some implementations of the method, deploying the device can comprise expanding the device proximal to the neck of the aneurysm and extending the first and second ends of the device into the efferent vessels. Further, the midsection of the device can act as a scaffolding to inhibit dislodging of objects into the afferent and efferent vessels.

In some implementations of the method, deploying the device can comprise expanding the device distal to the neck of the aneurysm and extending the first end and the second ends of the device within the aneurysm. Further, the first and second ends of the device can act as a scaffolding to inhibit dislodging of objects out of the neck of the aneurysm.

Further, in some implementations of the method, deploying the device can comprise expanding the device distal to the neck of the aneurysm and extending the first and second ends of the device at or near the neck of the aneurysm. Additionally, portions of the device near the first and seconds ends can act as a scaffolding to inhibit dislodging of objects into the afferent and efferent vessels.

In accordance with some embodiments, an intraluminal device is provided that can comprise a midsection and a plurality of stents extending from the midsection. Each of the stents can be configured to comprise a plurality of filaments coupled at the midsection and extending separately from the midsection towards a stent end and coupled at the stent end. In some embodiments, the plurality of stents can be configured to flex away from each other during expansion of the stents from a compressed state to an expanded state.

In some embodiments, the device can be configured to treat an aneurysm located at a junction of a bifurcation having an afferent and efferent vessels by acting as a scaffolding to inhibit dislodging of objects from within the aneurysm to the afferent and efferent vessels and to permit perfusion to the efferent vessels.

The device can be configured such that one or more portions proximate to the midsection can be porous. Further, the device can also be configured such that one or more portions proximate to stent can be porous.

For example, the device can be configured such that porosity distally increases from a proximal region to the midsection. Thus, the porosity of portions proximate to the midsection can be relatively higher than portions proximate to stent ends. In some embodiments, the device can be configured such that porosity distally decreases from the midsection to a distal region towards the stent end. Thus, the porosity of portions proximate to the stent ends can be relatively higher than portions proximate to the midsection.

In some embodiments, end portions of the device can be configured to act as a scaffolding to inhibit dislodging or prolapse of objects out of the neck of the aneurysm and to permit perfusion of fluid to the efferent vessels. The device can be configured such that the porosity of portions proximate to the midsections is relatively higher than the porosity of portions proximate to the stent ends. However, in some embodiments, the device can be configured to comprise relatively low or no porosity in portions proximate to the midsection.

Additionally, the midsection portions of the device can be configured to act as a scaffolding to inhibit dislodging or prolapse of objects out of the neck of the aneurysm and to permit perfusion of fluid to the efferent vessels. The device can also be configured such that the porosity of portions proximate to the stent ends is relatively higher than the porosity of the portions proximate to the midsection. Thus, in some embodiments, the device can be configured to comprise relatively high porosity in portions proximate to the stent ends. The device can also be configured to comprise relatively low or no porosity in portions proximate to the stent ends. In some embodiments, the device can be generally bow-tie shaped in the expanded state.

The device can also be configured such that a first stent of the plurality of stents deviates from a horizontal line by a first angle and a second stent of the plurality of stents deviates from the horizontal line by a second angle. For example, the first angle can be substantially equal to the second angle. Further, the first angle and the second angle can be different. Additionally, at least one of the first angle or the second angle can be negative.

In some embodiments, each stent of the plurality of stents can be spaced about the midsection from another stent of the plurality of stents by an interstent angle. For example, the interstent angle can be greater than 0°. Further, the interstent angle can be less than 180°. Additionally, the interstent angle can be between about 45° and about 180°. In some embodiments, the interstent angle can be between about 135° and about 180°.

Further, in some embodiments, the plurality of stents can be equally spaced about the midsection. However, in some embodiments, the plurality of stents may not be equally spaced about the midsection.

The device can also be configured such that the plurality of filaments extends from the midsection towards at least one said stent end. For example, the plurality of filaments can extend from the midsection towards at least one stent end in a generally straight configuration. Additionally, the plurality of filaments can extend from the midsection towards at least one said stent end in a generally twisted configuration. Further, at least one of the plurality of filaments can comprise a shape memory material. In some embodiments, at least one of the plurality of filaments can comprise a shape memory metal. Additionally, at least one of the plurality of filaments can comprise a radiopaque material. At least one of the plurality of filaments can also comprise a self-expanding material. Furthermore, at least one of the plurality of filaments can comprise a bioabsorbable polymer. In some embodiments, the plurality of filaments can be coupled at the stent ends by a bioabsorbable coupling. The plurality of filaments can also be coupled at the midsection by a bioabsorbable coupling.

In some embodiments, the plurality of stents can be substantially similarly shaped. The plurality of stents may also not be substantially similarly shaped. For example, at least one of the plurality of stents can be hexagonal-shaped in profile. At least one of the plurality of stents can be generally pumpkin-shaped. At least one of the plurality of stents can be generally football-shaped. At least one of the plurality of stents can be generally acorn-shaped. At least one of the plurality of stents can be generally spiral-shaped. At least one of the plurality of stents can be generally diamond-shaped.

The device can be configured to be substantially symmetrical about the midsection. However, in some embodiments, the device may not be substantially symmetrical about the midsection.

The device can also be configured to comprise a covering on at least a portion of the device. For example, the portion can comprise the midsection of the device. In some embodiments, the portion can also comprise the stent ends.

In accordance with some embodiments, the plurality of stents can be fabricated separately and then joined. Further, the plurality of stents can be integrally fabricated from a sheet or tube. At least one of the plurality of stents can be woven from individual filaments.

The device can be configured such that the plurality of stents is two stents. Further, the plurality of stents can be three stents. The plurality of stents can also comprise more than three stents.

The device can be delivered to a target site by a catheter and deployed or released therefrom. In some embodiments, device can be configured to be deployed at a junction of a bifurcation having an afferent vessel, efferent vessel and an aneurysm having a neck and a fundus. For example, the device can be releasable from a catheter by electrolytic, chemical, or mechanical detachment. In some embodiments, end portions of the device can be configured to conform to a neck of an aneurysm. Further, the midsection of the device can be configured to conform to a neck of an aneurysm. The device can be configured to self-expand from a compressed state to an expanded state upon deployment from at least partially inside a catheter to outside a the catheter. Further, the device can be configured to reduce the effective size of the neck of the aneurysm.

For purposes of summarizing the inventions and the advantages achieved over the prior art, certain objects and advantages of the inventions are described herein. Of course, it is to be understood that not necessarily all such objects or advantages need to be achieved in accordance with any particular embodiment. Thus, for example, those skilled in the art will recognize that the inventions can be embodied or carried out in a manner that achieves or optimizes one advantage or group of advantages as taught or suggested herein without necessarily achieving other objects or advantages as may be taught or suggested herein.

All of these embodiments are intended to be within the scope of the inventions herein disclosed. These and other embodiments will become readily apparent to those skilled in the art from the following detailed description having reference to the attached figures, the inventions not being limited to any particular disclosed embodiment(s).

BRIEF DESCRIPTION OF THE DRAWINGS

These and other features, aspects, and advantages of the present disclosure are described with reference to the drawings of certain embodiments, which are intended to illustrate certain embodiments and not to limit the inventions.

FIG. 1 illustrates an embodiment of a side wall aneurysm.

FIG. 2 illustrates an embodiment of a bifurcation having an aneurysm.

FIGS. 4B and 4C illustrates embodiments of a bifurcation having an aneurysm treated with embolization coils and tubular remodeling devices.

FIG. 5A illustrates an embodiment of a vascular remodeling device.

FIG. 5B illustrates the vascular remodeling device of FIG. 5A in a different orientation.

FIG. 5C depicts an outline of the side view of the device of FIG. 5A.

FIG. 5D depicts an outline of the top view of the device of FIG. 5A.

FIGS. 6A-6D illustrate an embodiment of a method for treating an aneurysm using the device of FIG. 5A.

FIGS. 7A-7C illustrate another embodiment of a method for treating an aneurysm using the device of FIG. 5A.

FIGS. 8A-8E illustrate another embodiment of a method for treating an aneurysm using the device of FIG. 5A.

DETAILED DESCRIPTION

Figure 3A:
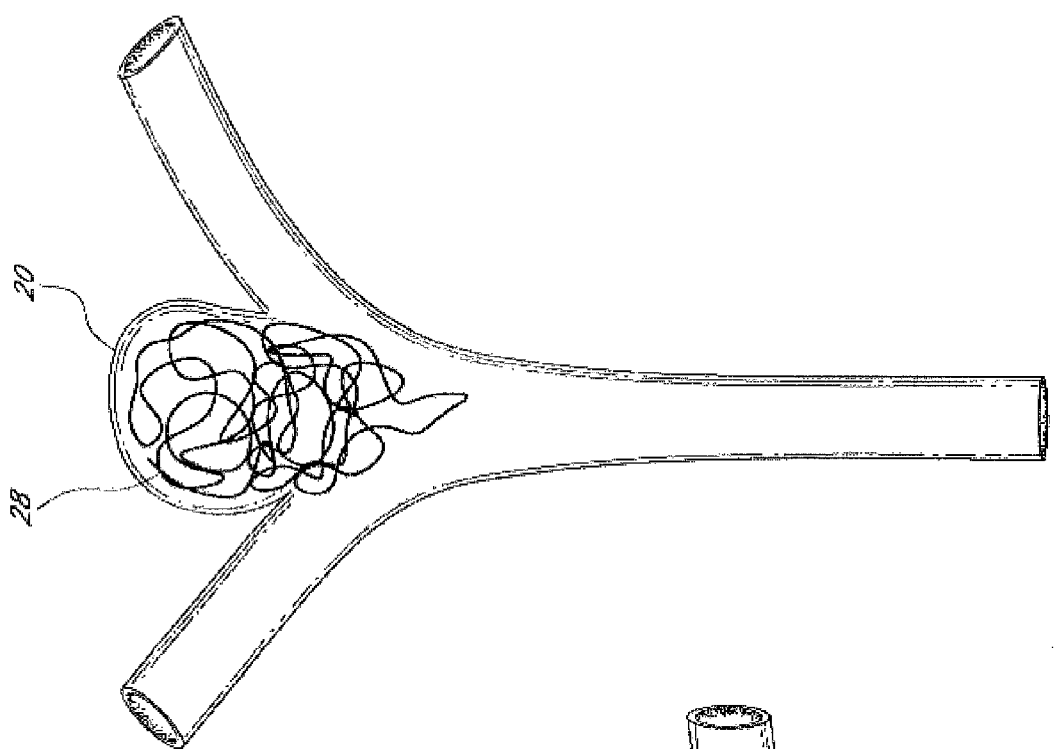
FIG. 3A illustrates an embodiment of a side wall aneurysm with herniating embolization coils.
Figure 3B:
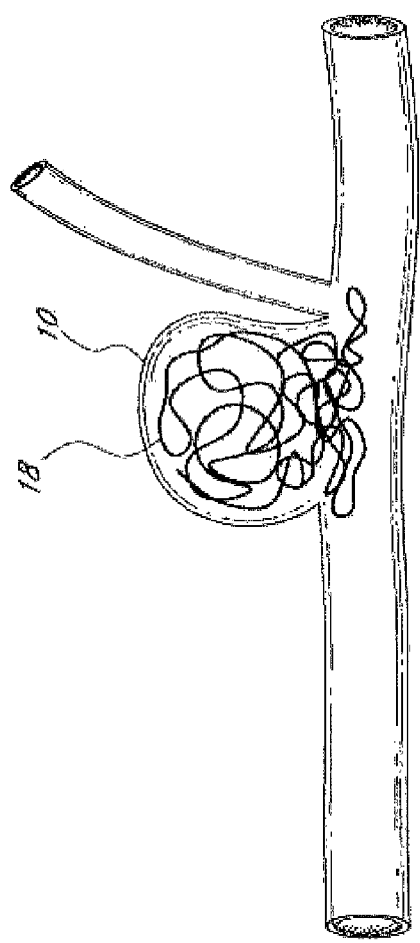
FIG. 3B illustrates an embodiment of a bifurcation having an aneurysm with herniating embolization coils.

Although certain embodiments and examples are described below, those of skill in the art will appreciate that the inventions extends beyond the specifically disclosed embodiments and/or uses and obvious modifications and equivalents thereof. Thus, it is intended that the scope of the inventions herein disclosed should not be limited by any particular embodiments described below.

Various embodiments disclosed herein provide for a vascular remodeling device and related methods. As discussed herein, the vascular remodeling device can be used facilitate the treatment of an aneurysm. Embodiments of the devices and methods disclosed herein can enable the effective treatment of an aneurysm at a bifurcating vessel while allowing perfusion of blood to the vessels. The device can be configured such that it is more compliant than the vasculature in which it is deployed in order to allow the device to be somewhat misshapen after being deployed. Further, the phrase "bow-tie shaped" can describe the shape of the device when in an expanded state outside of vasculature. The device can also be shape set into various configurations. Further, the phrase "bow-tie shaped" may not refer to all configurations as heat set.

The device can comprise a first end, a second end, and a midsection. In some embodiments, the vascular remodeling device can be generally bow-tie shaped. The phrase "bow-tie shaped" can refer to the general shape and of the device as having a narrowed central midsection. In some embodiments, the narrowed central midsection can interconnect or couple portions of the stent together. For example, first and second stents (e.g., stent-like structures, cage-like structures) can be coupled together at a point or along a length or region (e.g., the midsection). As discussed and illustrated further herein, the midsection of the device can facilitate compliance and maneuverability of the device within the vasculature. Thus, while some embodiments can comprise generally symmetrical sections of the device that meet at a midsection of the device, various other embodiments can be formed in order to implement aspects disclosed herein.

FIGS. 5A and 5B illustrate an embodiment of a vascular remodeling device 50. The illustrated embodiment of the vascular remodeling device 50 is generally bow-tie shaped. As noted above, one of the advantageous aspects of such a configuration is that the device 50 can be more compliant than the vasculature in which it is deployed such that it can be somewhat misshapen after being deployed.

Referring to the embodiment of FIGS. 5A and 5B, the device 50 comprises a first end 53, a second end 55, and a midsection 51. As noted above, the phrase "bow-tie shaped" can refer to a first stent 57 and a second stent 58 (e.g., stent-like structures, cage-like structures) coupled at a point or along a length or region (e.g., the midsection 51). In the embodiment illustrated in FIGS. 5A and 5B, the stents 57, 58 are substantially similarly sized and shaped and the device 50 is generally symmetrical about the midsection 51.

In some embodiments, the device can be generally asymmetrical about the midsection. For example, the stents 57, 58 can comprise the same shape, but have different sizes. For another example, the stents 57, 58 can have the same size, but comprise different shapes. For yet another example, the stents 57, 58 can comprise different shapes and have different sizes.

In some embodiments, the shape and/or size of the stent(s) can be based on, for example, vascular dimensions and deployment orientation. For example, the midsection 51 can comprise the point, line, area, or region at which the two stents 57, 58 are coupled. In some embodiments, the device 50 can be connected to a catheter at the midsection 51. The midsection 51 of the device 50 can comprise a lead or tail 64, which can be used for releasing and/or retracting the device after deployment, as described herein.

The first stent and/or the second stent can each comprise a plurality of filaments. For example, referring to the embodiment illustrated in the figures, the first stent 57 comprises a plurality of filaments 59 extending separately from the midsection 51 towards the first end 53. The second stent 58 also comprises a plurality of filaments 59 extending separately from the midsection 51 towards the second end 55. In some embodiments, the filaments 59 can extend outwardly from the midsection 51 in a substantially symmetrical manner (e.g., having evenly spaced and/or uniform filaments). However, filaments 59 can extend outwardly from the midsection 51 in a substantially asymmetrical manner (e.g., having unevenly spaced and/or non-uniform filaments). For example, in some embodiments, the filaments 59 extend in a twisted configuration from the midsection 51 towards the first end 53 and the second end 55. In some embodiments, the filaments 59 extend in a straight configuration from the midsection 51 towards the first end 53 and the second end 55.

In some embodiments, deployment of the device can include the use of one or more guidewires. For example, the one or more guidewires can be routed to a bifurcation or anatomy proximate thereto, and then the device 50 (e.g., the stent 57 and/or the stent 58) can be tracked over the guidewire(s). Accordingly, in some embodiments, the stents 57, 58 can comprise filaments 59 letter configured in a straight configuration, which can thus advantageously reduce friction between the filaments 59 and the guidewire(s) extending through one or both of the stents 57, 58 during deployment of the device 50. Reduced friction during deployment can increase accuracy of the deployed position of the device 50, for example as discussed herein (e.g., as described with respect to FIGS. 6A-8E). The filaments 59 can be more compliant than the vasculature in which it is deployed such that it can be somewhat misshapen after being deployed, and the shapes and configurations described herein refer to the filaments 59 when the device 50 is in an expanded state outside the vasculature.

In some embodiments, the filaments can be arranged into a mesh configuration (e.g., braided, criss-cross, woven). The filaments can be individual filaments that are joined (e.g., braided, woven, attached, glued, coupled) or can be cut from a tube or sheet, creating a desired pattern or configuration. In some embodiments, the first stent and the second stent can both be cut from the same tube or sheet, and the midsection can comprise a substantially uncut section of the tube or sheet. In some embodiments, the filaments can be coupled (e.g., by adhering, welding, soldering, not being cut apart, coupling using a separate component, combinations thereof, and the like) at the first end and at the second end.

In some embodiments, the cross-sectional perimeter or circumference of the first and/or second stents can vary along the length(s) thereof. For example, as illustrated in the figures, the cross-sectional perimeter or circumference of the stent 57 or spacing between the filaments 59 of the stent 57 increases from the midsection 51 towards a point or plane 80 along the length of the stent 57 and decreases from the point 80 towards the first end 53, and the cross-sectional perimeter or circumference of the stent 58 or spacing between the filaments 59 of the stent 58 increases from the midsection 51 towards a point or plane 81 along the length of the stent 58 and decreases from the point 81 towards the second end 55. The rate of increase and/or decrease may not be uniform along the length of the stent 57 and/or the stent 58. The increase and/or decrease can be linear, multi-linear (e.g., as illustrated in FIGS. 5A and 5B), curved, combinations thereof, and the like.

For example, in the embodiments illustrated in FIGS. 5A and 5B, the cross-sectional perimeter or circumference of the stent 57 or spacing between the filaments 59 of the stent 57 increases from the midsection 51 towards the point or plane 82 at a first rate in the first midsection portion 52 and at a second rate from the first midsection portion 52 towards the point 80. Further, the cross-sectional perimeter or circumference of the stent 58 or spacing between the filaments 59 of the stent 58 increases from the midsection 51 towards the point or plane 83 at a first rate in the second midsection portion 54 and at a second rate from the second midsection portion 54 towards the point 81.

Low porosity at the first and second end portions 60, 61 can enhance the ability of the device 50 to act as a scaffolding to inhibit the dislodging or prolapse of objects (e.g., coils, thrombi) from an aneurysm, for example in the configuration of FIG. 5B. Low porosity at the first and second midsection portions 52, 54 can enhance the ability of the device 50 to act as a scaffolding to inhibit the dislodging or prolapse of objects (e.g., coils, thrombi) from an aneurysm, for example in the configuration of FIG. 5A. High porosity at the first and second end portions 60, 61 can enhance the ability of the device 50 to allow perfusion to efferent vessels, for example in the configuration of FIG. 5A. High porosity at the midportions 84, 85 can enhance the ability of the device 50 to allow perfusion to efferent vessels, for example in the configuration of FIG. 5B.

The first stent 57 and/or second stent 58 can be generally diamond shaped, as shown in FIG. 5A. As noted above, other shapes are also possible (pumpkin, acorn, spiral, football, etc.). The first stent 57 and the second stent 58 can have the same shape or different shapes. The first stent 57 and the second stent 58 can have the same size or different sizes. As depicted in FIG. 5C, in some embodiments, each stent 57, 58 can define a hexagon in an outline of the side profile of the device 50. Other shapes are possible (e.g., teardrop, parallelogram, ellipse, rhombus, pentagon, quadrilateral, etc.). The first stent 57 and the second stent 58 can have the same shape outline or different shape outlines.

In some embodiments, the device 50 can comprise more than two stents. For example, in some embodiments, the device 50 can be configured to be deployed at a junction of a trifurcation having an afferent vessel, three efferent vessels, and an aneurysm. In certain such embodiments, the device 50 comprises three stents, each configured to be positioned in an efferent vessel. Other numbers of stents are possible, either based on the number of efferent vessels or otherwise (e.g., a device comprising three stents can be used at a bifurcation (e.g., in the orientation of FIG. 5B)), a device comprising four stents can be used at a bifurcation (e.g., two stents in the orientation of FIG. 5A and two stents in the orientation of FIG. 5B).

FIG. 5C depicts an outline of a side view of device 50. As shown in FIG. 5C, in some embodiments, the stents 57, 58 can be set to cause lines 62, 63, connecting the midsection 51 to the first and second ends 53, 55, respectively, to be at angles α, β from horizontal. In some embodiments, the stents 57, 58 can be set in such a configuration using heat setting (e.g., causing the lines 62, 63 to be above the horizontal line H-H by bending the stent 57 at the midsection 51 at an angle α between about 0 degrees and about 90 degrees and bending the stent 58 at the midsection 51 at an angle β between about 0 degrees and about 90 degrees). In some embodiments, the configuration of guidewires used to deploy stents 57, 58 causes the stents 57, 58 to be set in a particular configuration (e.g., having angles α, β). Other means of setting the stents 57, 58 in various configurations are also possible.

For example, the stents 57, 58 can be formed individually and can then be coupled so that lines 62, 63 are at angles α, β from horizontal. In some embodiments, the device 50 can be heat set in an orientation, such as in FIG. 5A, and be deployed in a stressed state, as illustrated in FIG. 5B. The angles α, β can be the same or different. In some embodiments, the first and second stents 57, 58 can be set in an orientation that causes the lines 62, 63 to deviate from the horizontal by bending at the midsection 51 to cause the first and second ends 53, 55 to be below the horizontal line H-H (e.g., bending the line 62 at the midsection 51 at an angle −α between about 0 degrees and about 90 degrees and bending the line 63 at the midsection 51 at an angle −β between about 0 degrees and about 90 degrees). The angles −α, −β can be the same or different. In some embodiments, setting the stents 57, 58 to cause the lines 62, 63 to be at negative angles from horizontal can provide good anchoring of a device 50 deployed as depicted in FIG. 5B at least partially in an aneurysm. In some embodiments, heat setting the stents 57, 58 to cause the lines 62, 63 to be at negative angles from horizontal can reduce the likelihood of a device 50 deployed as depicted in FIG. 5A of puncturing or otherwise disrupting an aneurysm or vasculature (e.g., because the device 50 can flex at the midpoint 51 away from an aneurysm).

In some embodiments, the first and second stents 57, 58 can be set in an orientation that causes the lines 62, 63 to deviate from the horizontal at opposing angles. For example the line 62 can deviate from the horizontal at an angle α and the line 63 can deviate from the horizontal at an angle −β. The angles α, −β can be the same or different. In some embodiments, deviation from the horizontal can be based on size, shape, etc. of each of the stents 57, 58. For example, in a device in which the stents 57, 58 are asymmetric, one stent can be bent more than the other stent to compensate for the asymmetry. Stents of a device 50 comprising more than two stents can also be set to deviate from the horizontal as described herein.

For example, in a device comprising three stents, each stent can deviate from the horizontal by a different angle. In some embodiments, all three stents can deviate from the horizontal by the same angle. In some embodiments, two of the stents deviate from the horizontal by the same angle and the third stent can deviate from the horizontal by a different angle.

In another example, in a device comprising four stents (e.g., two stents in the orientation of FIG. 5A and two stents in the orientation of FIG. 5B), two of the stents can deviate from the horizontal by a positive first angle and the other two stents can deviate from the horizontal by a negative second angle. In some embodiments, deviation from the horizontal can be based on angles of certain vasculature. The term "horizontal" is being used as a baseline which can vary (e.g., depending on the orientation of device). For example, the horizontal line H-H can be drawn at any arbitrary vertical position, and is not necessarily at the distal end of the tail 64 as shown in FIG. 5C. The stents can be more compliant than the vasculature in which they are deployed such that they can be somewhat misshapen after being deployed, and that the configurations described herein can refer to the configurations of the stents 57, 58 when in an expanded state outside of the vasculature or to an intended configuration of the stents 57, 58 when deployed within the vasculature.

The stents can be set in various configurations using a variety of different means. For example, FIG. 5D depicts an outline of a top view of the device 50. As shown in FIG. 5D, in some embodiments, the stents 57, 58 can be set to cause lines 65, 66 connecting the midsection 51 to the first and second ends 53, 55 respectively, to be separated by an interstent angle γ. In some embodiments, the stents 57, 58 are set in such a configuration using heat setting. In some embodiments, the configuration of guidewires used to deploy stents 57, 58 causes the stents 57, 58 to be set in a particular configuration (e.g., having an angle γ).

Other means of setting the stents in various configurations are also possible. For example, referring again to the embodiment illustrated in the figures, the stents 57, 58 can be formed individually and can then be coupled so that the lines 65, 66 are at an angle γ. The stents 57, 58 can be substantially equally spaced about the midsection 51 (e.g., spaced about 180° apart as shown in FIG. 5D). However, in some embodiments, the stents may not be equally spaced about the midsection.

In some embodiments, the interstent angle γ can be between about 5° and about 180°. In some embodiments, the interstent angle γ can be between about 45° and about 180°. In some embodiments, the interstent angle γ can be between about 135° and about 180°. Further, for a device 50 comprising two stents 57, 58, the interstent angle γ can be measured on either side of the lines 65, 66.

In some embodiments, setting the stents to be more closely spaced about the midsection can reduce the size of the profile (e.g., a dimension measure from the first end 53 to the second end 55) of the device. For example, the configuration of the embodiment illustrated in FIG. 5B demonstrates a close spacing of the stents 57, 58 about the midsection 51 of the device 50. The orientation of the stents 57, 58 around the midsection 51 can be based on angles of vasculature or dimensions of aneurysms.

In accordance with some embodiments, a device with a small size in profile can be preferred to treat an aneurysm with a small neck. Stents of a device comprising more than two stents can also be set to deviate from one another as described herein. For example, stents of a device comprising three stents can be substantially equally spaced about the midsection (e.g., spaced about 120° apart). For another example, in a device comprising three stents, the stents may not be equally spaced about the midsection (e.g., having an angle of about 90° between a first and a second stent, an angle of about 90° between the second and a third stent, and angle of about 180° between the third and the first stent). For yet another example, stents of a device comprising four stents (e.g., two stents in the orientation of FIG. 5A and two stents in the orientation of FIG. 5B) can comprise a first angle (e.g., about 30°) between a first and a second stent (e.g., the first and second stents in the orientation of FIG. 5B) and can comprise an second angle (e.g., about 80°), larger than the first angle, between the first stent and a third stent and the second stent and a fourth stent (e.g., the third and fourth stents in the orientation of FIG. 5A). Other angles are also possible. The stents of the device can be configured to be more compliant than the vasculature in which they are deployed such that they can be somewhat misshapen after being deployed, and that the configurations described herein can refer to the configurations of the stents when in an expanded state outside of the vasculature or to an intended configuration of the stents when deployed within the vasculature.

An outer surface of the device can comprise or be covered by one or more filaments. In some embodiments, a percentage of the outer surface of the device 50 or a portion thereof (e.g., at the first and second end portions 60, 61, at the first and second midsection portions 52, 54) covered by the filaments 59 is greater than or equal to about 3%. In some embodiments, a percentage of the outer surface of the device 50 or a portion thereof (e.g., at the first and second end portions 60, 61, at the first and second midsection portions 52, 54) covered by the filaments 59 is between about 3% and about 15% (e.g., about 5%). In some embodiments, a percentage of the outer surface of the device 50 or a portion thereof (e.g., at the first and second end portions 60, 61, at the first and second midsection portions 52, 54) covered by the filaments 59 is between about 3% and about 25%. Other percentages of the outer surface of the device 50 or a portion thereof covered by the filaments 59 are also possible.

The device can comprise a plurality of perforations or cells between the filaments. For example, the embodiment illustrated in figures shows that the device 50 comprises a plurality of perforations or cells 66 between the filaments 59. In some embodiments, a percentage of the outer surface of the device 50 or a portion thereof (e.g., at the first and second end portions 60, 61, at the first and second midsection portions 52, 54) covered by the cells 66 or porosity can be less than or equal to about 97%. In some embodiments, a percentage of the outer surface of the device 50 or a portion thereof (e.g., at the first and second end portions 60, 61, at the first and second midsection portions 52, 54) covered by the cells 66 or porosity can be between about 85% and about 97% (e.g., about 95%). In some embodiments, a percentage of the outer surface of the device 50 or a portion thereof (e.g., at the first and second end portions 60, 61, at the first and second midsection portions 52, 54) covered by the cells 66 or porosity can be between about 75% and about 97%. Other porosities are also possible.

In some embodiments, the porosity of the device can vary based on the location along the device. For example, as illustrated in the figures, the porosity of the device 50 can increase moving from the midsection 51 towards the points 80, 81 along the length of first and second stents 57, 58. Further, the porosity of the device 50 can distally decrease moving from points 80, 81 towards the first and second ends 53, 55.

High porosity at the midportions 84, 85 of the stents 57, 58 can provide good fluid flow to efferent vessels, for example in the configuration of FIG. 5B. High porosity at the first and second end portions 60, 61 can provide good fluid flow to efferent vessels, for example in the configuration of FIG. 5A. Low porosity proximate to the first and second ends 53, 55 (e.g., at the first and second end portions 60, 61) of the device 50 can provide good scaffolding properties, for example in the configuration of FIG. 5B. Low porosity proximate to the midsection 51 (e.g., at the first and second midsection portions 52, 54) of the device 50 can provide good scaffolding properties, for example in the configuration of FIG. 5A.

According to some embodiments, the device can be integrally formed from a continuous sheet of material. However, the device can also be formed using separate components that are attached to each other to form the device.

For example, the entire device 50 (e.g., both of the first and second stents 57, 58 of the device 50) can be integrally fabricated from a metallic sheet. A laser or electrochemical etch can cut out portions of a metallic sheet, leaving a plurality of cells or perforations 66 and defining a desired configuration of filaments 59 (e.g., straight, twisted, criss-cross). The sheet can be uncut towards ends of the sheet or portions of the sheet forming the ends 53, 55 of the device 50 to create the first and second ends 53, 55 of the device 50. The sheet can be uncut towards an intermediate portion of the sheet to couple the filaments 59 to create the midsection 51 of the device 50. The dimensions of the filaments 59 or perforations 66 can be uniform throughout the device 50 or can vary depending on location. For example, the widths of the filaments 59 can increase to reduce porosity and decrease to increase porosity. Dimensions can be selected, for example to accommodate certain vasculature. In embodiments in which the stents 57, 58 are integrally formed, the stents 57, 58 can have the same size and shape or different sizes or shapes.

In some embodiments, the device can be shaped or shape set using heat treatment. For example, the sides of the sheet can be rolled towards each other to create a more tubular profile. For another example, the filaments can be shaped to expand radially outwardly at different longitudinal positions along the first and second stents of the device. For yet another example, the first stent can be shaped (e.g., by bending at the midsection) to deviate from a baseline configuration (e.g. horizontal) by an angle $\alpha$, and the second stent can be shaped to deviate from a baseline configuration by an angle $\beta$, as described herein (e.g., with respect to FIG. 5C).

The shape setting process can include several steps comprising, for example, successive shapes, using appropriate tolling to stretch and confine the cut sheet into a new shape during the heat treatment. At the end of each heat treatment step, the cut sheet can assume the shape in which it was confined during the heat treatment process. The final shapes and sizes can be obtained by several such steps. The final shape can include a slit along the length of one or both of the stents, or the edges can be welded or otherwise joined together by other methods. If the sheet was cut during forming the midsection and/or the first and second ends, the filaments of the first and second stents can be coupled (e.g., by adhering, welding, soldering, combinations thereof, and the like) at the midsection, the first end, and/or the second end. Devices described herein can also be formed using a cut metallic tube (e.g., a laser cut hypotube) that is reshaped after being cut, although the properties of the initial tube and the pattern of the cut can be different.

In some embodiments, the first stent can be integrally fabricated from a sheet and a second stent can be integrally fabricated from a different sheet, and the two stents can thereafter be coupled (e.g., by adhering, welding, soldering, combinations thereof, and the like) at a midsection of the device. Further, more than two stents can be coupled together in some embodiments. For example, the stent 57 can be integrally fabricated from a sheet and the stent 58 can be integrally fabricated from a different sheet, and the two stents 57, 58 can thereafter be coupled (e.g., by adhering, welding, soldering, combinations thereof, and the like) at a midsection 51 of the device 50. Further, more than two stents can be coupled together in some embodiments. In certain such embodiments, each stent 57, 58 can be fabricated through cutting and forming operations, as discussed below.

For example, in accordance with some embodiments, a laser or electrochemical etch can cut out portions of a metallic sheet, leaving a plurality of cells or perforations 66, and defining a desired filament 59 configuration (e.g., as described herein, straight, twisted, braided, woven). The dimensions of the filaments 59 or perforations 66 can be uniform throughout each of the stents 57, 58 or can vary depending on location. For example, the widths of the filaments 59 can increase to reduce porosity and decrease to increase porosity. Dimensions can be selected, for example to accommodate certain vasculature. The sheets can each be uncut at one end to create the first end 53 of the stent 57 and the second end 55 of the stent 58. In some embodiments, the sheets are each uncut at the other end to create the ends of the stents 57, 58 that will be positioned proximate to or at the midsection 51 of the device 50. In some embodiments, the filaments 59 at the proximal ends of the stents 57, 58 (e.g., not the first and second ends 53, 55) are uncoupled after the cutting process. The uncoupled filaments 59 of the stent 57 can be coupled to the uncoupled filaments of stent 58, creating a midsection 51 and joining the first stent 57 and the second stent 58. The stents 57, 58 can be reshaped using heat treatment as described herein before or after being coupled at a midsection 51.

In some embodiments, and with reference to the figures for clarity, the device 50 can be configured to comprise a plurality of individual filaments 59 (e.g., wires, ribbons) that are coupled at an intermediate point of the filaments 59 to form a midsection 51 and at the ends of the filaments 59 to form first and second ends 53, 55 of the device 50. Portions of the filaments 59 extending beyond the ends 53, 55 can be trimmed.

The filaments of the device can undergo heat treatment as described herein. For example, the filaments 59 can be shaped to expand radially outwardly at different longitudinal positions along the first and second stents 57, 58. In some embodiments, the first and second stents 57, 58 can be fabricated separately and can each comprise a plurality of individual filaments 59. The filaments 59 can be coupled at one end of each of the first stent 57 and the second stent 58 to form first and second ends 53, 55. The filaments can be coupled at the other end of each stent 57, 58, at which end the two stents 57, 58 can be coupled to one another to form the midsection 51 of the device 50.

In some embodiments, the filaments 59 can be coupled at one end of each of the stent 57 and the stent 58 to form first and second ends 53, 55 and are not coupled at the other end of each stent 57, 58. The uncoupled filaments 59 of each stent can then be joined, coupling the filaments 59 and the stents 57, 58 and creating a midsection 51 of the device 50. Variations and combinations of the fabrication methods described herein are also possible.

For example, in some embodiments, one stent (e.g., the first stent 57) comprises individual filaments 59 coupled at one or both ends and the other stent (e.g., the second stent 58) is cut from a sheet, and the two stents 57, 58 are joined together to create a midsection 51 of the device 50. For another example, in some embodiments, one or both stents 57, 58 can be cut from a sheet (e.g., forming perforations 66 and filaments 59) and can also comprise additional filaments 59 (e.g., comprising wires, ribbons) attached thereto.

In some embodiments, at least one of the filaments 59 can comprise a self-expanding and/or a shape-memory material (e.g., comprising Nitinol, CoCr alloy, MP35N®, L605, etc.), and the device 50 is self-expanding under certain conditions (e.g., not restrained by a catheter).

In some embodiments, at least one of the filament can comprise a different material than others of the filaments (e.g., some filaments can comprise Nitinol and some filaments can comprise Nitinol and platinum).

In some embodiments, at least one of the filaments can comprise a radiopaque material (e.g., platinum). In some embodiments, at least one of the filaments 59 can comprise a radiopaque material (e.g., platinum) at least partially wrapped (e.g., coiled) around a self-expanding material (e.g., Nitinol). In some embodiments, at least one of the filaments 59 can comprise a self-expanding material with a radiopaque core (e.g., Nitinol with a platinum core) or a radiopaque coating (e.g., Nitinol coated with platinum, tantalum, etc. by physical vapor deposition, chemical vapor deposition, plating, etc.). The amount and type of radiopaque material used can depend, inter alia, on price, desired level of radiopacity, mechanical properties of the radiopaque material, and corrosion properties of the radiopaque material. In certain embodiments, the filaments 59 have a substantially circular or ovoid cross section (e.g., embodiments in which the filaments 59 comprise separate wires). In some embodiments, the filaments 59 have a substantially rectangular or flat cross section (e.g., embodiments, in which the filaments 59 comprise ribbons or uncut portions of a metallic sheet or tube). Other shapes of filaments 59 and combinations of shapes of filaments 59 are also possible.

In accordance with some embodiments, the device can optionally comprise one or more radiopaque markers. For example, the device 50 can comprise one or more radiopaque markers proximate to the first end 53 and/or the second end 55 to aid in positioning the device 50 at the junction of a bifurcation. In some embodiments, the device 50 can comprise a radiopaque marker proximate to midsection 51. In some embodiments, the device 50 can comprise one or more radiopaque markers proximate to or along the plane 80 and/or proximate to or along the plane 81. In some embodiments, the device 50 can comprise one or more radiopaque markers proximate to or along the plane 82 and/or proximate to or along the plane 83. In certain embodiments, radiopaque markers can extend at least partially into an aneurysm when the device 50 is positioned at the junction of a bifurcation. In certain embodiments, radiopaque markers can extend at least partially into efferent vessels when the device 50 is positioned at the junction of a bifurcation. In some embodiments, radiopaque markers can comprise a sleeve positioned or wrapped around the filaments 59, thereby coupling the filaments 59. Other configurations and locations for radiopaque markers are possible.

In some embodiments, the device can comprise a bioabsorbable polymer. For example, the filaments 59 and/or a coupling (e.g., a separate component) that joins the filaments 59 at the midsection 51 and/or at one or both of the first and second ends 53, 55 of the device 50 can comprise a bioabsorbable polymer. In certain embodiments, the filaments 59 and/or coupling can comprise polyglycolic acid (PGA), polylactic acid (PLA), poly(lactic-co-glycolic acid) (PLGA), poly-epsilon-caprolactone (PCL), naturally derived bioabsorbable polymers (NDB), or combinations thereof. Other polymers are also possible. PGA, PLA, PLGA, PCL, and NDB are all bioabsorbable; however they have different rates of bioabsorption. The bioabsorption rates of a single polymer can also vary based on, for example, blood characteristics, blood flow, coupling dimensions, etc. PLA has the longest bioabsorption rate. In some embodiments, the bioabsorption rate of PLA is at least about ten months. In some embodiment, the bioabsorption rate of PLA is at least about one year. In some embodiments, the bioabsorption rate of PLA is at least about fourteen months. In some embodiments, the bioabsorption rate of PLA is between about ten months and about fourteen months (e.g., about one year). In some embodiments, the bioabsorption rate of PGA is between about 1 week and about 3 weeks. In some embodiments, the bioabsorption rate of PGA is between about 2 weeks and about 4 weeks. The bioabsorption rates of PLGA, PCL, and NDB are generally between the bioabsorption rates of PLA and PGA, and can depend on parameters such as, for example, molecular weight (e.g., generally the higher the molecular weight, the longer the bioabsorption rate), structure (e.g., depending on the arrangement of repeating units), etc. of the polymer. In some embodiments, PLGA, PCL, and NDB can have a bioabsorption rate between about 4 weeks and about 1 year. The bioabsorption rate generally refers to the time it takes for the polymer to lose about 50% of strength. The polymer(s) used in the device 50 can be selected based on the amount of time an aneurysm can take to thrombose (e.g., based on fundus size, neck width, etc.) For example, if an aneurysm is expected to take one month to thrombose and the device 50 is expected to persist through thrombosis but not long thereafter, PGA can be selected. The polymer(s) used in the device 50 can be selected based on the amount of time an aneurysm can take to obliterate (e.g., based on fundus size, neck width, etc.). For example, if an aneurysm is expected to take on year to obliterate and the device 50 is expected to persist through obliteration, PLA can be selected. Other polymers or combinations of polymers can be selected based on the particular aneurysm to be treated and the desired action and/or persistence of the device 50 with respect to the aneurysm. Other selection criteria are also possible. Different combinations of polymers with different rates of bioabsorption can allow for selection of a desired rate of bioabsorption for the device 50. For example, a device 50 comprising filaments 59 and/or a coupling comprising a combination of PGA and PLA can have a rate of bioabsorption of a device 50 or certain portions of the device 50 in between the rate of bioabsorption of a device 50 or portions of a device 50 comprising only PGA or only PLA.

The device can comprise a compressed state and an expanded state. The compressed state can refer to the device 50 while it is being actively constricted (e.g., within a catheter). The properties of the device 50 or the filaments 59 of the device 50 (e.g., material, dimensions, rigidity) can enable the device 50 to be compressed. The expanded state can refer to the device 50 when deployed within the vasculature.

In some embodiments, the first stent 57 and/or the second stent 58 can comprise a central filament that can be used to reshape the stent 57, 58 while in an expanded state. The central filament can be rigid (e.g., having a size and/or shape configured to allow pushing and pulling without significant deformation of the central filament). The central filament can be used to adjust a distance between the midsection 51 and the first end 53 and/or the second end 55 of the device by pulling the first end and/or second end 55 along the central filament towards the midsection 51 or by pushing the midsection 51 along the central filament towards the first end and/or second end 55. The device 50 can comprise a mechanism for maintaining the device 50 in the reshaped state.

In some embodiments, the device can comprise a covering, a mesh, additional filaments, etc. in order to provide a desired porosity at a given location of the device. For example, the device 50 can comprise a covering, a mesh, additional filaments, etc. at the first and/or second end portions 60, 61 and/or the first and/or second midsection portions 52, 54 (e.g., depending on method of deployment) in order to decrease porosity at the first and second ends 51, 53 and/or at the first and second midsection portions 52, 54. For example, where the first and second end portions 60, 61 are configured to act as a scaffolding to inhibit the prolapse of objects from the neck of the aneurysm, the first and/or second end portions 60, 61 can comprise a covering, mesh, or additional filaments. For another example, where the first and second midsection portions 52, 54 are configured to act as a scaffolding to inhibit the prolapse of objects from the neck of the aneurysm, the first and/or second midsection portions 52, 54 can comprise a covering, mesh, or additional filaments. Decreased porosity at the first and second end portions 60, 61 and/or the first and second midsection portions 52, 54 can enhance the ability of the device 50 to act as a scaffolding to inhibit the prolapse of objects (e.g., thrombi, coils) from the neck of an aneurysm and to reduce the effective size of the neck of the aneurysm. In some embodiments, portions of the device not acting as a scaffolding can be substantially devoid of a covering, mesh, additional filaments, etc., which can better allow perfusion of fluid.

In certain embodiments, the first stent 57 and the second stent 58 can be configured to be positioned at a junction of a bifurcation (e.g., a neurovascular bifurcation) comprising at least one afferent vessel, efferent vessels, and an aneurysm having a fundus and a neck. For example, in some embodiments, the first stent 57 and/or the second stent 58 is/are suitably dimensioned to fit in a junction of a bifurcation, a neck of an aneurysm at a bifurcation, and/or in an efferent vessel of a bifurcation. For example, at least one of the stents 57, 58 having a diameter between about 1 mm and about 12 mm. In some embodiments, the diameter can be between about 1 mm and about 6 mm. Further, in some embodiments, the diameter can be between about 3 mm and about 4 mm. For example, in some embodiments, the diameter can be less than about 12 mm. Furthermore, in some embodiments, the diameter can be less than about 6 mm. Moreover, in some embodiments, the diameter can be greater than about 1 mm. In some embodiments, the diameter can be greater than about 2 mm. Additionally, some embodiments can be configured to comprise combinations of diameters, such as those mentioned above and the like.

For another example, in some embodiments, the device 50 can be less rigid than a junction of a bifurcation (e.g., due to the number of filaments 59, the material of the filaments 59, the thickness of the filaments 59, the spacing of the filaments 59, the shape of the filaments 59, the shape of the stents 57, 58, combinations thereof, and the like). In certain embodiments, the device 50 is configured to act as a scaffolding to inhibit or prevent dislodging or prolapse of objects (e.g., embolization coils, embolic fluid, thrombi, etc.) out of a neck of an aneurysm. For example, in some embodiments, the filaments 59 are dense enough at or proximate to the neck of the aneurysm that objects generally cannot pass. In certain embodiments, the device 50 is configured to permit perfusion of fluid (e.g., blood) to efferent vessels of a bifurcation.

FIG. 6A illustrates an initial configuration of an embodiment of a method for treating an aneurysm 20 using a system comprising the device 50 and a catheter 72. FIG. 6A illustrates a confluence of afferent and efferent vessels or "junction" at a bifurcation 70 having an aneurysm 20. In some embodiments, the vasculature can be neurovascular or cranial (e.g., a basilar tip aneurysm). A catheter 72 (e.g., a microcatheter), at least partially containing a constricted or compressed device 50, is also shown in the afferent vessel. For the sake of clarity, the device 50 is also shown within the catheter. The device 50, in the compressed state within the catheter 72, is folded so that the first and second ends 53, 55 are distal to the midsection 51. The catheter 72 is small enough and flexible enough to be routed through the vasculature and situated proximate to the aneurysm 20 (e.g., as depicted in FIG. 6A). The device 50 can be pre-loaded into the catheter 72 or can be inserted from the proximal end of the catheter 72 after the catheter 72 has been routed (e.g., using a guidewire) through the vasculature to the bifurcation 70. The configuration of the device 50 and the catheter 72 depicted in FIG. 6A can be used as a starting point for different embodiments of methods for treating an aneurysm 20 using a system comprising the device 50 and a catheter 72.

Figure 6C:
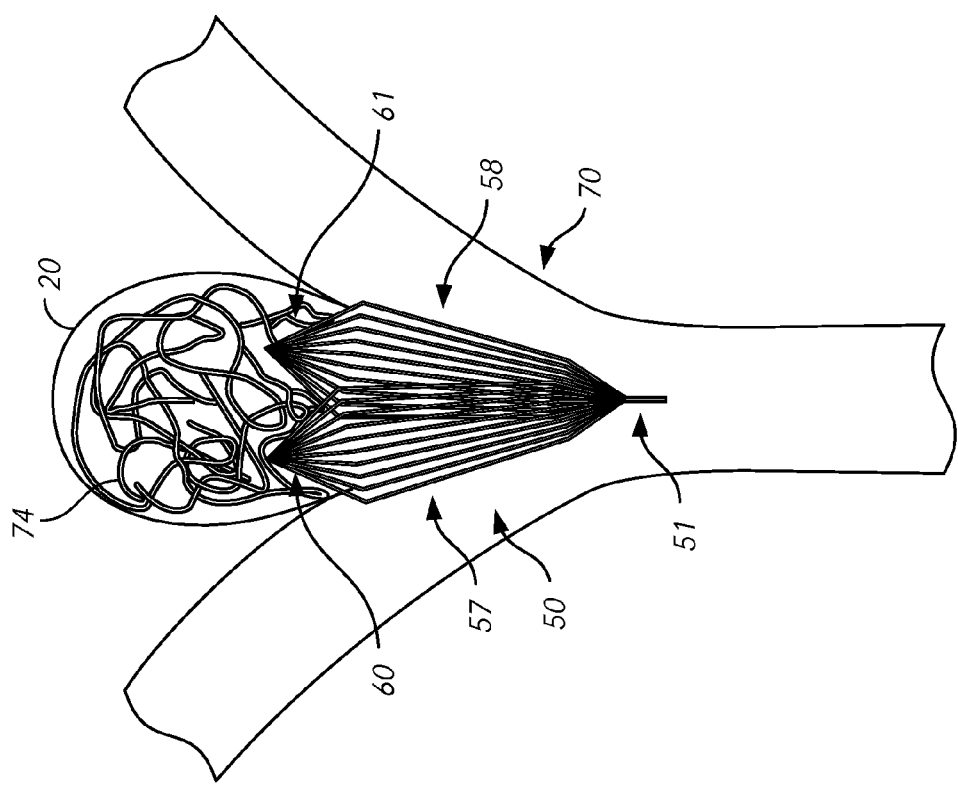
Figure 6D:
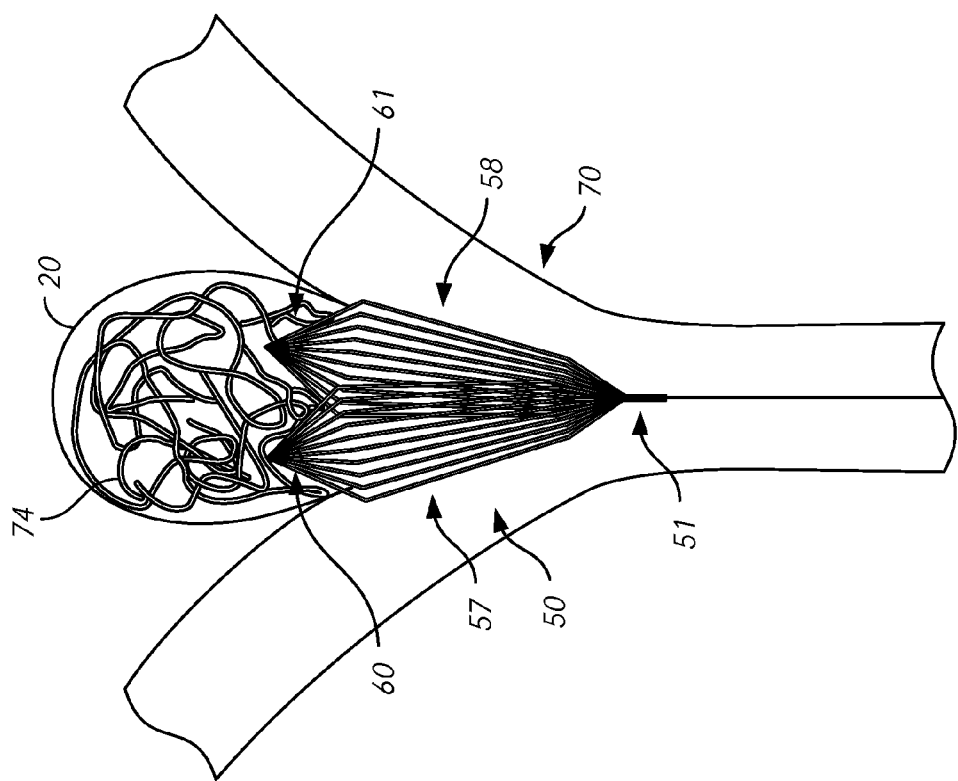

For example, FIGS. 6B-6D illustrate an embodiment for treating an aneurysm 20 using a system comprising the device 50 and a catheter 72. The catheter 72 can be distally advanced from the position shown in FIG. 6A until the distal tip of the catheter 72 is placed in the aneurysm 20 or at the neck of the aneurysm 20. The device 50 can then be pushed out of the distal end of the catheter 72 (e.g., by being pushed out with a plunger, by retracting the catheter 72 while the device 50 remains stationary, combinations thereof, and the like) at least partially within the aneurysm 20 or at the neck of the aneurysm 20.

FIG. 6B illustrates the bifurcation 70 after the device 50 has been deployed from the catheter 72 at the junction of the bifurcation 70. After being at least partially deployed from the catheter 72, the device 50 can expand. In some embodiments, the device 50 comprises a self-expanding and/or a shape-memory material that automatically expands towards an uncompressed state or expands towards an uncompressed state upon the application of warm fluid (e.g., saline). Other expansion mechanisms are also possible. The device 50 can substantially conform to the shape of the junction of the bifurcation 70 (e.g., not substantially including portions extending into the afferent and efferent vessels) and/or to the neck of the aneurysm 20, and can lock into place across the neck of the aneurysm 20. The device 50 can be heat set so that the first and second stents 57, 58 can bias away from one another when in a compressed configuration (e.g., as shown in FIG. 6A).

Upon deployment of the device 50 at the bifurcation 70, the first and second stents 57, 58 bias away from one another and lock into place across the neck of the aneurysm 20. The device 50 can be deployed at least partially within the aneurysm 20 (e.g., a portion of the first and second ends portions 60, 61 can be partially within the aneurysm 20). In some embodiments, the points 80, 81 (FIG. 5A) can be positioned in the fundus of the aneurysm 20. In some embodiments, the points 80, 81 (FIG. 5A) can be positioned outside of the aneurysm 20 (e.g., as depicted in FIG. 6B). The device 50 can act as a scaffolding to inhibit or prevent dislodging or prolapse of objects such as embolization coils 74 (FIG. 6C) and/or thrombi out of the aneurysm 20. More particularly, in the embodiment illustrated in FIGS. 6A-6D, the first and second end portions 60, 61 of the device 50 can act as a scaffolding to inhibit or prevent dislodging or prolapse of objects such as the embolization coils 74 and/or thrombi out of the aneurysm 20. The device 50 can reduce the effective size of the neck of the aneurysm 20. The device 50 can also allow perfusion of fluid (e.g., blood) from the afferent vessel to the efferent vessels. In some embodiments, the device 50 can be reshaped after deployment (e.g., to increase the cross-sectional area of one or both of the stents 57, 58).

Embolization coils can be inserted into the fundus of the aneurysm before, during, and/or after deployment of the device.

For example, in embodiments in which embolization coils 74 are inserted in the fundus of the aneurysm during or after deployment of the device 50, the insertion of the embolization coils 74 can be through the first and second end portions 60, 61. FIG. 6C depicts the aneurysm 20 after embolization coils 74 have been inserted into the fundus of the aneurysm 20. The embolization coils 74 can be a single embolization coil or other embolic material (e.g., Onyx® liquid embolic material). In some embodiments, the embolization coils 74 can be inserted in the fundus of the aneurysm 20 using the catheter 72. In some embodiments, the embolization coils 74 can be inserted in the fundus of the aneurysm 20 using a different catheter. In certain such embodiments, a guidewire can be used to guide both catheters.

In some embodiments, the device 50 is released from the catheter 72 after deployment or after redeployment. The device 50 can be released from the catheter 72 (e.g., by a mechanical, chemical, or electrolytic release mechanism), thereby leaving or permanently positioning the device 50 at the junction of the bifurcation, as shown in FIG. 6D.

The term "permanently" does not mean that the device 50 is impossible to remove and/or reposition a later time. In some embodiments, the delivery catheter or a different catheter can be used to retrieve (e.g., by pulling on a tail) or reposition the device 50. In certain embodiments, the device 50 can be retracted into a catheter (e.g., the catheter 72, a different catheter) after being deployed. The device 50 can then be repositioned or can be completely removed from the body, for example prior to delivery of a new device (e.g., a different device 50). Once the user is satisfied with the repositioned properties of the device 50 (e.g., size, position, rotation, shape, interaction with the vessels, interaction with the aneurysm 20, interaction with the coils 74, etc.), the device 50 can be released.

FIGS. 7A-7C depict another embodiment of a method for treating an aneurysm 20 using a system comprising the device 50 and a catheter 72. The method depicted in FIGS. 7A-7C can comprise initially routing the catheter 72 through the vasculature to a location proximate to the bifurcation 70 (e.g., as described herein with respect to FIG. 6A). The catheter 72 can be distally advanced from the position shown in FIG. 6A until the tip of the catheter 72 is placed in the aneurysm 20 or at the neck of the aneurysm 20. FIG. 7A depicts the bifurcation 70 after the device 50 has been deployed from the catheter 72 at the junction of the bifurcation 70. As shown in FIG. 7B, the method depicted in FIGS. 7A-7C results in the device 50 being positioned at a more proximal location than the location of the device 50 resulting from the method depicted in FIGS. 6B-6D. As such, the catheter 72 used to deploy the device 50 can be located at a more proximal position during deployment.

After being at least partially deployed from the catheter 72, the device 50 can expand. In some embodiments, the device 50 comprises a self-expanding and/or a shape-memory material that automatically expands towards an uncompressed state or expands towards an uncompressed state upon the application of warm fluid (e.g., saline). Other expansion mechanisms are also possible. The device 50 can substantially conform to the shape of the junction of the bifurcation 70 (e.g., not substantially including portions extending into the afferent and efferent vessels) and/or to the neck of the aneurysm 20, and can lock into place across the neck of the aneurysm 20. The device 50 can be heat set so that the first and second stents 57, 58 bias away from one another when in a compressed configuration.

Upon deployment of the device 50 at the bifurcation 70, the first and second stents 57, 58 can bias away from one another and lock into place across the neck of the aneurysm 20. The device 50 can be deployed at least partially within the aneurysm 20 (e.g., the first and second stent ends 53, 55 can be partially within the aneurysm 20). In some embodiments, the ends 53, 55 can be positioned in the fundus of the aneurysm 20. The device 50 can act as a scaffolding to inhibit or prevent dislodging or prolapse of objects such as embolization coils 74 (FIG. 7B) and/or thrombi into the afferent vessel 77 or the efferent vessels 78, 80. In the embodiment illustrated in FIGS. 7A-7C, the first and second end portions 60, 61 of the device 50 act as a scaffolding to inhibit or prevent dislodging or prolapse of objects such as the embolization coils 74 and/or thrombi into the afferent vessel 77 or efferent vessels 78, 80. Although objects can be dislodged out of the neck of the aneurysm, the objects cannot be dislodged into the afferent vessel 77 or the efferent vessels 78, 80. The device 60 reduces the effective size of the neck of the aneurysm 20. The device 50 also allows perfusion of fluid (e.g., blood) from the afferent vessel 77 to the efferent vessels 78, 80. In some embodiments, the device 60 can be reshaped after deployment (e.g., to increase the cross-sectional area of one or both of the stents 57, 58).

Embolization coils 74 can be inserted into the fundus of the aneurysm before, during, and/or after deployment of the device 50. FIG. 7B depicts the aneurysm 20 after embolization coils 74 have been inserted into the fundus of the aneurysm 20. In embodiments in which embolization coils 74 are inserted in the fundus of the aneurysm during or after deployment of the device 50, the insertion of the embolization coils 74 can be through the first and/or second end portions 60, 61. The embolization coils 74 can be a single embolization coil or other embolic material (e.g., Onyx® liquid embolic material). In some embodiments, the embolization coils 74 are inserted in the fundus of the aneurysm 20 using the catheter 72. In some embodiments, the embolization coils 74 can be inserted in the fundus of the aneurysm 20 using a different catheter. In certain such embodiments, one or more guidewires can be used to guide both catheters.

In some embodiments, the device 50 can be released from the catheter 72 after deployment or after redeployment. The device 50 can be released from the catheter 72 (e.g., by a mechanical, chemical, or electrolytic release mechanism), thereby leaving or permanently positioning the device 50 at the junction of the bifurcation, as shown in FIG. 7C. As noted above, the term "permanently" does not mean that the device 50 is impossible to remove and/or reposition a later time using any of the methods or structures discussed herein.

Figure 8D:
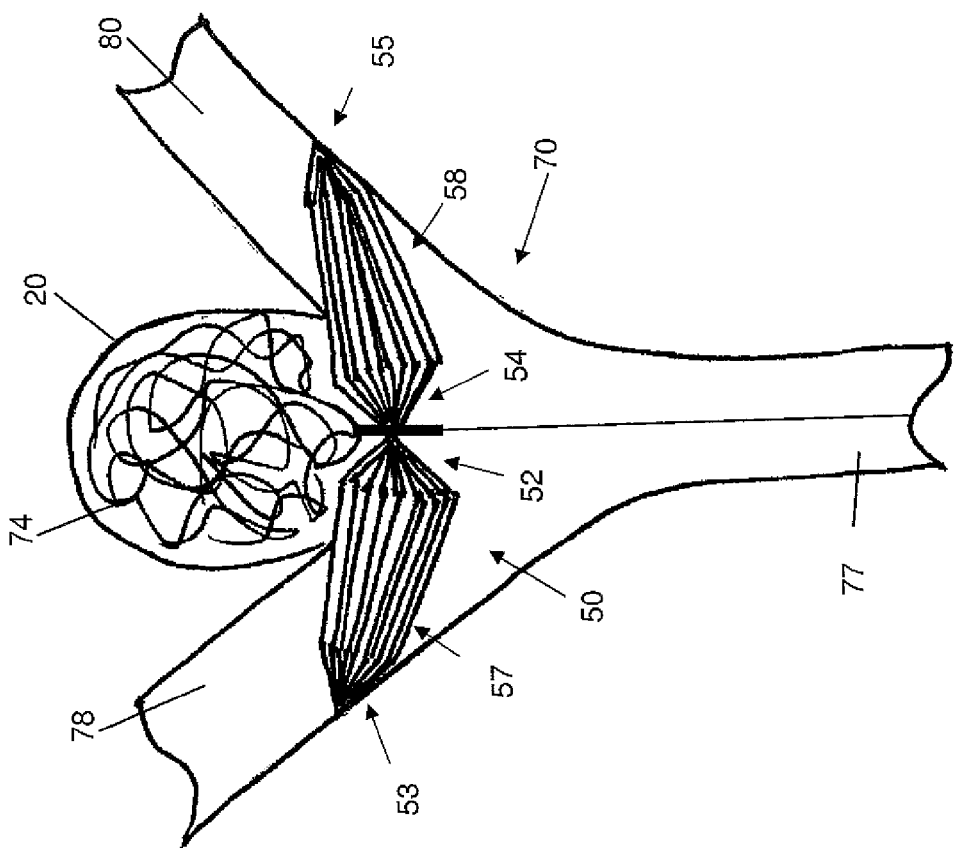

FIGS. 8A-8E depict another embodiment of a method for treating an aneurysm 20 using a system comprising the device 50 and a catheter 72. The method depicted in FIGS. 8A-8E can comprise initially routing one or more guidewires 71, 73 (e.g., one guidewire per stent 57, 58) through the vasculature as shown in FIG. 8A. A first guidewire 71 and a second guidewire 73 can be routed through the vasculature to a location within the efferent vessels 78, 80. The proximal ends of the guidewires 71, 73 can then be threaded through the first and second stents 57, 58, respectively. The first and second stents 57, 58 can then be pushed into the proximal end of a catheter 72, which can then be tracked along the guidewires 71, 73 to a location proximate to the bifurcation 70. Alternatively, the catheter 72 can have already been tracked along the guidewires 71, 73 to a location proximate to the bifurcation 70. The proximal ends of the guidewires 71, 73 can then be threaded through the first and second stents 57, 58, respectively, and the stents 57, 58 can then be tracked along the guidewires 71, 73 within the catheter 72 to a location proximate the bifurcation 70.

FIG. 8B depicts the first guidewire 71 and the second guidewire 73 extending from the distal ends of the first stent 57 and the second stent 58, respectively, while the stents 57, 58 remain in a compressed state within the catheter 72. FIG. 8B illustrates the device 50 as it is being deployed from a compressed state within the catheter 72 (e.g., by being pushed out with a plunger, by retracting the catheter while the device 50 remains stationary, combinations thereof, and the like) at the junction of the bifurcation 70. In some embodiments, the catheter 72 can deploy the device 50 from a more proximal position (e.g., within the junction, distal to the ostium of the afferent vessel, proximal to the aneurysm 20, proximal to the ostia of the efferent vessels 78, 80) than the position from which the device 50 was deployed in the embodiment depicted in FIGS. 6B-6D and FIGS. 7A-7C. This deployment position can enable the stents 57, 58 to bias into the efferent vessels 78, 80.

The device 50 can be heat set so that the stents 57, 58 bias away from one another when in a compressed configuration (e.g., as shown in FIG. 8A). In such embodiments, the first and second guidewires 71, 73 can be threaded through the first and second stent 57, 58 so that the guidewires 71, 73 extend from the stents 57, 58 on the outside of first and second ends 53, 55 or on the sides that are farthest from one another (e.g., on the right side of stent end 55 and on the left side of stent end 53 as depicted in FIG. 8A). This position of the guidewire can enable the first and second stents 57, 58 to stay relatively centered along the guidewires 71, 73 and to not bias into the walls of the efferent vessels 78, 80.

As the device 50 is pushed out of the catheter 72 along the guidewires 71, 73, the position of the guidewires 71, 73 can shift as they are influenced by the device 50. The first and second stents 57, 58 can be deployed along the guidewires 71, 73 into the efferent vessels 78, 80 and the midsection 51 can be deployed at the neck of the aneurysm 20. As the device 50 leaves the catheter 72, the device can begin to expand as shown in FIG. 8B. In some embodiments, the device 50 comprises a self-expanding and/or a shape-memory material that automatically expands towards an uncompressed state or expands towards an uncompressed state upon the application of warm fluid (e.g., saline). Other expansion mechanisms are also possible. The method described herein can also be performed without using guidewires to guide the first and second stents 57, 58. For example, in embodiments in which the first and second stents 57, 58 are configured to bias away from one another, upon deployment from a catheter, the first and second stents 57, 58 can bias into the efferent vessels 78, 80 without the aid of guidewires.

Figure 8C:
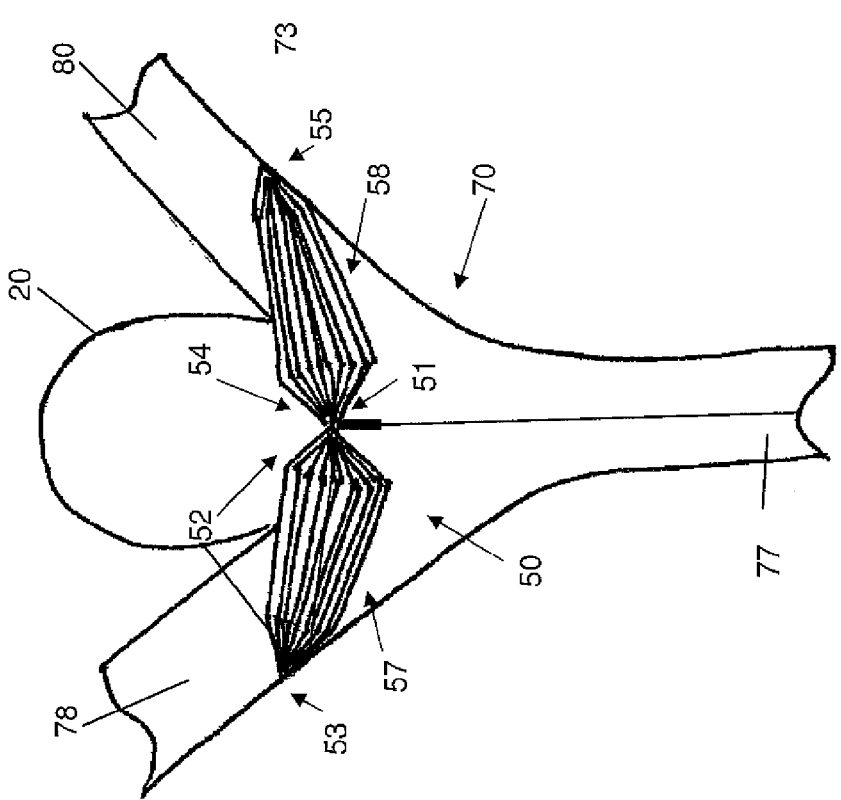

FIG. 8C depicts the device 50 locked into place across the neck of the aneurysm 20 with the midsection 51 positioned across the neck of the aneurysm 20 and the first and second ends 53, 55 extending into the efferent vessels 78, 80. FIG. 8C depicts the guidewires 71, 73 as having been removed after positioning of the device. In some embodiments, the guidewires 71, 73 can remain in position (e.g., in embodiments in which the device 50 is to be repositioned or a new device 50 is to be deployed, in embodiments in which another device (e.g., a drug delivery catheter) is tracked over one or both of the guidewires, etc.). The device 50 can substantially conform to the shape of the junction of the bifurcation 70 and/or to the neck of the aneurysm 20. The device 50 at least partially covers the neck of the aneurysm 20 and the afferent and efferent vessels, but does not need to divert flow.

In some embodiments, the device 50 can be deployed at least partially within the aneurysm 20 (e.g., the midsection 51 can be partially within the aneurysm 20). In some embodiments, the midsection 51 can be outside of the aneurysm 20 (e.g., as depicted in FIG. 8C). In some embodiments, the points 82, 83 (FIG. 5A) can be in the fundus of the aneurysm 20. In some embodiments, the points 82, 83 (FIG. 5A) can be outside of the aneurysm 20 (e.g., as depicted in FIG. 8C).

The device 50 acts as a scaffolding to inhibit or prevent dislodging or prolapse of objects such as embolization coils 74 (FIG. 8D) and/or thrombi into the afferent vessel 77 or the efferent vessels 78, 80. In the embodiment illustrated in FIGS. 8A-8D, the first and second midsection portions 52, 54 act as a scaffolding to inhibit or prevent dislodging or prolapse of objects such as embolization coils and/or thrombi into the afferent vessel 77 or the efferent vessels 78, 80. Although objects can be dislodged out of the neck of the aneurysm, the objects cannot be dislodged into the afferent vessel 77 or the efferent vessels 78, 80. The device 50 reduces the effective size of the neck of the aneurysm 20. The device 50 also allows perfusion of fluid (e.g., blood) from the afferent vessel 77 to the efferent vessel 78, 80. In some embodiments, the device 50 can be reshaped after deployment (e.g., to increase the cross-sectional area of one or both of the stents 57, 58).

As noted above, embolization coils can be inserted into the fundus of the aneurysm before, during, and/or after deployment of the device.

For example, FIG. 8D depicts the aneurysm 20 after embolization coils 74 have been inserted into the fundus of the aneurysm 20. In embodiments in which embolization coils 74 are inserted in the fundus of the aneurysm during or after deployment of the device 50, the insertion of the embolization coils 74 can be through the first and second midsection portions 52, 54. The embolization coils 74 can be a single embolization coil or other embolic material (e.g., Onyx® liquid embolic material). In some embodiments, the embolization coils 74 can be inserted in the fundus of the aneurysm 20 using the catheter 72. In some embodiments, the embolization coils 74 can be inserted in the fundus of the aneurysm 20 using a different catheter. In certain such embodiments, a guidewire can be used to guide both catheters.

In some embodiments, the device 50 is released from the catheter 72 after deployment or after redeployment. The device 50 can be released from the catheter 72 (e.g., by a mechanical, chemical, or electrolytic release mechanism), thereby leaving or permanently positioning the device 50 at the junction of the bifurcation, as shown in FIG. 8E. As noted above, the term "permanently" does not mean that the device 50 is impossible to remove and/or reposition a later time using any of the methods or structures discussed herein.

In certain embodiments, the filaments 59 and/or one or more couplings of the filaments 59 comprises a bioabsorbable polymer. This bioabsorbability can be advantageous in conjunction with permanent placement of the device 50. For example, after thrombosis of the aneurysm following treatment, the device 50 can no longer be needed to inhibit dislodging of material. Certain bioabsorbable embodiments of the device 50 can advantageously inhibit dislodging during thrombosis of the aneurysm, but bioabsorb when they can no longer be needed to inhibit dislodging.

Figure 9:
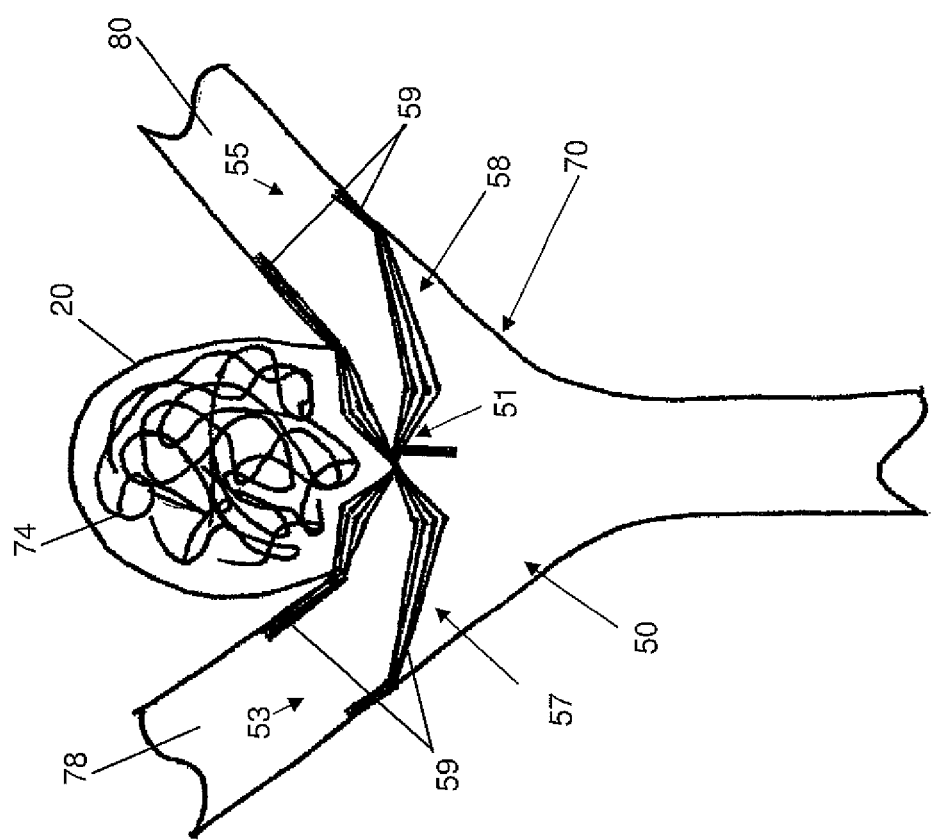
FIG. 9 illustrates another embodiment of a method for treating an aneurysm.

In some embodiments, the couplings of the filaments 59 at the first and second ends 53, 55 are configured to bioabsorb while the remainder of the device 50 persists. For example, the couplings can comprise a polymer with a faster rate of bioabsorption than the remainder of the device 50. For another example, the couplings can comprise a bioabsorbable polymer and the remainder of the device may not comprise a bioabsorbable polymer (e.g., comprising a shape-memory metal). Bioabsorption of the couplings can release the filaments 59 at the first and second ends 53, 55 to extend radially outwardly to the walls of the efferent vessels 78, 80, which can advantageously clear the interior section of the stents 57, 58 in the efferent vessels 78, 80, for example from the configuration of FIG. 8E to the configuration of FIG. 9, restoring normal blood flow therein (e.g., in embodiments in which the coupled ends 53, 55 can have allowed perfusion but altered blood flow).

In some embodiments, the coupling of the filaments 59 at the midsection 51 of the device 50 is configured to bioabsorb while the remainder of the device 50 persists. For example, the coupling can comprise a polymer with a faster rate of bioabsorption than the remainder of the device 50.

Figure 10:
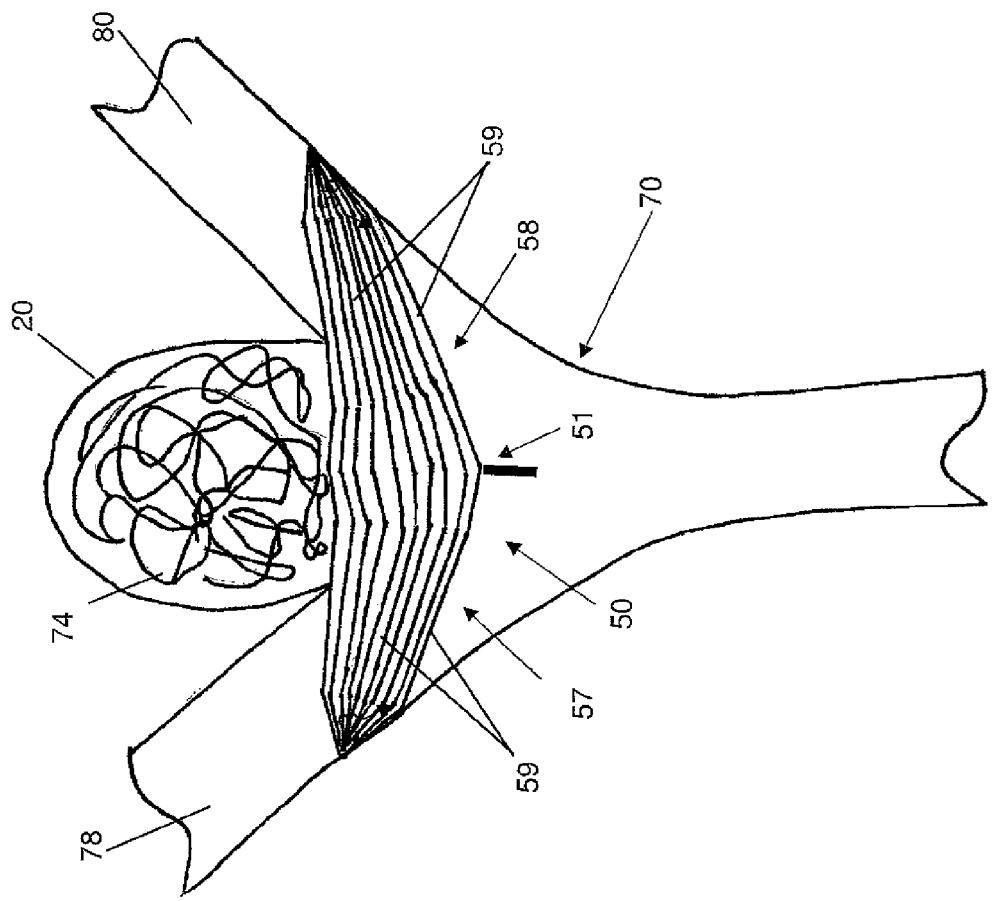
FIG. 10 illustrates another embodiment of a method for treating an aneurysm.

For another example, the coupling can comprise a bioabsorbable polymer and the remainder of the device 50 may not comprise a bioabsorbable polymer. Bioabsorption of the midsection 51 coupling can release the filaments 59 at the midsection 51 of the device 50 which can allow the filaments 59 to expand across the neck of the aneurysm, for example from the configuration of FIG. 8E to the configuration of FIG. 10. This expanded configuration of the filaments 59 can advantageously increase the scaffolding coverage provided by the device 50 as a greater surface area of the device 50 can be located at or near the neck of the aneurysm 20.

In some embodiments, the device 50 can comprise bioabsorbable couplings at the midsection 51 and the first and second ends 53, 55 of the device 50. For example, in embodiments of the device 50 comprising intertwined (e.g., braided, woven, criss-cross patterned, mesh patterned, etc.) filaments 59, bioabsorption of the couplings at the midsection 51 and stent ends 53, 55 couplings can advantageously increase the scaffolding coverage provided by the device 50 at the midsection 51 and can also allow the filaments to extend radially outwardly to the walls of the efferent vessels 78, 80 and can clear a portion of the stents 57, 58 from at least a portion of the efferent vessels 78, 80, restoring normal blood flow therein (e.g., in embodiments in which the coupled ends 53, 55 can have allowed perfusion but altered blood flow).

Bioabsorbability of the device 50, or portions of the device 50, can make permanent placement or release of the device 50 a less consequential procedure as the device 50 or portions thereof may not remain in the vasculature permanently or can remain with reduced impact.

Certain devices described herein can be advantageously used to treat aneurysms having a neck ratio (a ratio of fundus width to neck width) greater than about 2 to 1 and/or a neck width greater than about 4 mm. In treatment of such aneurysms, embolization coils can be prone to dislodging into parent vessels because the size and/or shape of the aneurysm is not conducive to maintaining the coils in their inserted locus. In certain such embodiments, embolization coils can be inserted in the fundus of the aneurysm after positioning a generally bow-tie shaped device so that the embolization coils do not have an opportunity to dislodge. Certain devices described herein can also be used to treat aneurysms having a neck ratio less than about 2 to 1 and/or a neck width less than about 4 mm. In certain such embodiments, embolization coils can be inserted in the fundus of the aneurysm before positioning a generally bow-tie shaped device.

Figure 4B:
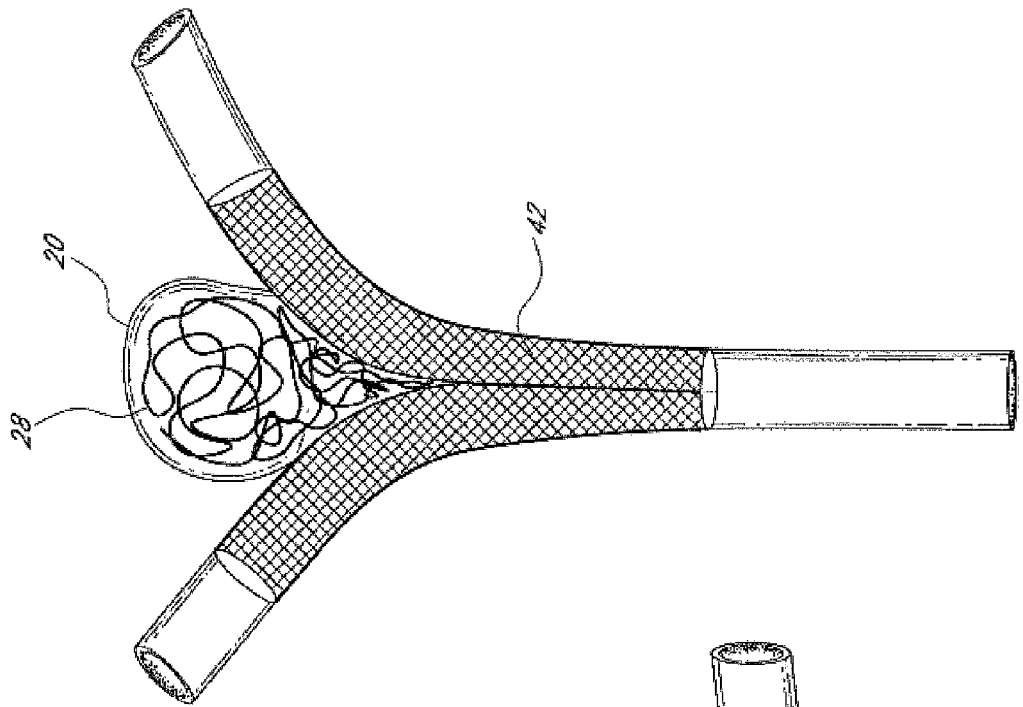
Figure 4A:
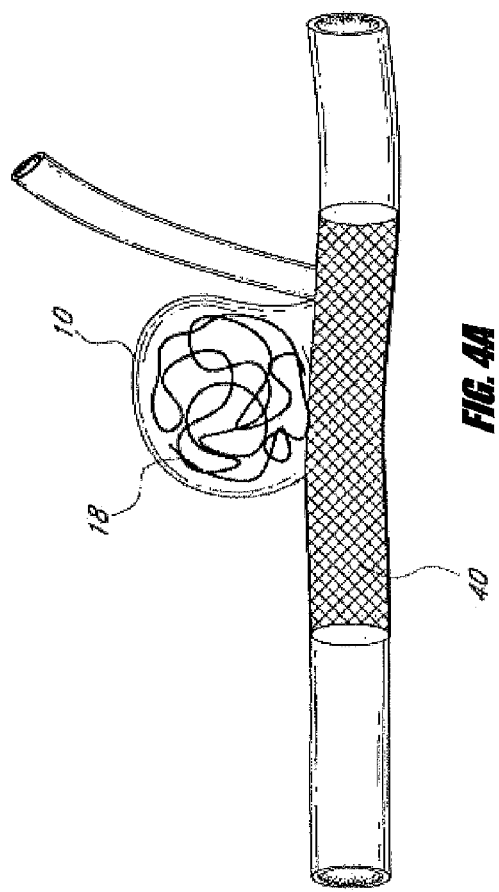
FIG. 4A illustrates an embodiment of a side wall aneurysm treated with embolization coils and a tubular remodeling device.

Certain devices described herein can advantageously comprise a single device placed at a junction of a bifurcation rather than a plurality of tubular devices (e.g., as shown in FIGS. 4B and 4C). Certain such devices can span a neck of an aneurysm as well as arterial ostia. Positioning such devices can be less complicated, thereby reducing risks associated with, for example, than ensuring that a tubular device is properly anchored in an afferent vessel and in an efferent vessel.

In some embodiments in which embolic material was previously inserted in an aneurysm but has been dislodged, certain devices described herein can be used as a "rescue device" to push the dislodged material back into the aneurysm and to act as a scaffolding to inhibit or prevent further dislodging or prolapse of the embolic material. In certain such embodiments, deployment of such devices can advantageously avoid traversal of the junction comprising the dislodged material by wires or a catheter (e.g., there is no need to traverse wires or a catheter past the junction into an efferent vessel for positioning of the device as is generally needed to position tubular devices such as the devices 42, 44 illustrated in FIGS. 4B and 4C), which can cause the dislodged material to become tangled and/or dislodged and which can cause rupture of the aneurysm.

Although these inventions have been disclosed in the context of certain embodiments and examples, it will be understood by those skilled in the art that the inventions extend beyond the specifically disclosed embodiments to other alternative embodiments and/or uses of the inventions and obvious modifications and equivalents thereof. In addition, while several variations of the embodiments of the inventions have been shown and described in detail, other modifications, which are within the scope of these inventions, will be readily apparent to those of skill in the art based upon this disclosure. It is also contemplated that various combinations or subcombinations of the specific features and aspects of the embodiments can be made and still fall within the scope of the inventions. It should be understood that various features and aspects of the disclosed embodiments can be combined with, or substituted for, one another in order to form varying modes of the embodiments of the disclosed inventions. Thus, it is intended that the scope of the inventions herein disclosed should not be limited by the particular embodiments described above.

What is claimed is:

1. An intraluminal device for use at a vessel bifurcation, the device comprising:
    a midsection;
    a tail coupled to the midsection and configured to permit pushing and pulling of the device within a catheter; and
    first and second stents each comprising a plurality of filaments coupled together at the midsection to form respective first and second proximal regions, the first and second stents extending separately from the midsection towards respective first and second distal regions, the first and second stent distal regions comprising respective first and second bioabsorbable couplings, wherein in a gathered configuration, (i) the plurality of filaments of the first stent converge to the first bioabsorbable coupling at the first distal region, and (i) the plurality of filaments of the second stent converge to the second bioabsorbable coupling at the second distal region, the first and second distal regions being configured to flex away from each other during expansion of the first and second stents from a compressed state to an expanded state, and wherein, upon bioabsorption of the first and second couplings, the first and second distal regions are expandable from the gathered configuration to a released configuration such that the pluralities of filaments at the first and second distal regions radially diverge for permitting normal blood flow through the bifurcation, and wherein the first and second stents alone support the device within efferent vessels of the bifurcation without the tail engaging an afferent vessel of the bifurcation.

2. The device of claim 1, wherein a porosity of each stent increases in a direction away from the midsection, from the first and second proximal region of each stent to midpoints of each of the first and second stents and distally decreases from the midpoints towards the first and second distal regions.

3. The device of claim 1, wherein the first and second distal regions are configured to act as a scaffolding to inhibit dislodging or prolapse of objects out of a neck of an aneurysm and to permit perfusion of fluid to the efferent vessels.

4. The device of claim 3, wherein the porosity of the first and second proximal regions is relatively higher than the porosity of the first and second distal regions.

5. The device of claim 1, wherein the first and second proximal regions are configured to act as a scaffolding to inhibit dislodging or prolapse of objects out of a neck of an aneurysm and to permit perfusion of fluid to the efferent vessels.

6. The device of claim 5, wherein the porosity of the first and second distal regions is relatively higher than the porosity of the first and second proximal regions.

7. The device of claim 1, wherein the first and second stents are spaced about the midsection from each other by an inter-stent angle of between about 45° and about 180°.

8. The device of claim 1, wherein the first and second stents are not equally spaced about the midsection.

9. The device of claim 1, wherein at least one of the plurality of filaments comprises a shape memory material.

10. The device of claim 1, wherein at least one of the plurality of filaments comprises a radiopaque material.

11. The device of claim 1, wherein at least one of the plurality of filaments comprises a bioabsorbable polymer.

12. The device of claim 1, wherein the only stents of the device are the first and second stents.

13. A method of treating an aneurysm at a junction of a bifurcation having an afferent vessel and efferent vessels, the aneurysm having a neck and a fundus, the method comprising:
    advancing a catheter proximate to the junction of the bifurcation, the catheter at least partially containing a vascular remodeling device in a compressed state, the device having a first stent, a second stent, a midsection coupled to the first and second stents, and a tail coupled to the midsection, wherein in the compressed state the first stent and the second stent are distal to the midsection and the tail is proximal to the midsection to permit pushing or pulling of the device within the catheter;
    pushing the tail to advance the device from at least partially inside the catheter to outside the catheter at the junction of the bifurcation, such that during deployment, the first and second stents are positioned within respective efferent vessels of the bifurcation and the first and second stents each self-expand to an expanded state to conform to the respective efferent vessel, and wherein first and second stents of the device support the device at the bifurcation by engaging the efferent vessels without the tail engaging an afferent vessel of the bifurcation; and
    permitting first and second bioabsorbable couplings, holding the first and second stents in gathered, tapered configurations, to bioabsorb such that the first and second stents radially expand within the efferent vessels of the bifurcation from the gathered, tapered configuration to diverge and contact walls of the efferent vessels.

14. The method of claim 13, further comprising retracting the device at least partially back inside the catheter.

15. The method of claim 14, further comprising re-deploying the device in at least one of a second orientation or a second position, such that during re-deployment, the device self-expands to the expanded state to conform to at least one of the junction of the bifurcation or the neck of the aneurysm.

16. The method of claims 13, further comprising detaching the device from the catheter.

17. The method of claim 13, further comprising inserting embolic material into the aneurysm.

18. The method of claim 17, wherein inserting embolic material into the aneurysm comprises inserting embolic coils into the aneurysm.

19. The method of claim 13, further comprising permitting expansion of the device proximal to the neck of the aneurysm, and wherein the midsection of the device acts as scaffolding to inhibit dislodging of objects into the afferent and efferent vessels.

20. The method of claim 13, further comprising permitting expansion of the device distal to the neck of the aneurysm, and wherein the portion of the device near the first and second stents act as scaffolding to inhibit dislodging of objects into the afferent and efferent vessels.

* * * * *